US009480588B2

United States Patent
Yan et al.

(10) Patent No.: US 9,480,588 B2
(45) Date of Patent: *Nov. 1, 2016

(54) BIODEGRADABLE ENDOPROSTHESES AND METHODS OF THEIR FABRICATION

(71) Applicant: Elixir Medical Corporation, Sunnyvale, CA (US)

(72) Inventors: John Yan, Los Gatos, CA (US); Vinayak Bhat, Cupertino, CA (US)

(73) Assignee: Elixir Medical Corporation, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/697,537

(22) Filed: Apr. 27, 2015

(65) Prior Publication Data

US 2016/0045343 A1 Feb. 18, 2016

Related U.S. Application Data

(63) Continuation-in-part of application No. 14/682,014, filed on Apr. 8, 2015, now Pat. No. 9,259,339, which is a continuation-in-part of application No. 14/461,159, filed on Aug. 15, 2014, now Pat. No. 9,119,905.

(51) Int. Cl.
*A61F 2/91* (2013.01)
*A61F 2/915* (2013.01)
(Continued)

(52) U.S. Cl.
CPC ............... *A61F 2/91* (2013.01); *A61B 90/39* (2016.02); *A61F 2/915* (2013.01); *A61L 31/06* (2013.01); *A61L 31/148* (2013.01); *A61L 31/18* (2013.01); *A61B 2090/3966* (2016.02);
(Continued)

(58) Field of Classification Search
CPC ............ A61F 2/89; A61F 2210/0004; A61F 2230/0069; A61F 2/07; A61F 2/01; A61F 2/06; A61F 2/82–2/958; A61F 2002/018; A61F 2002/06; A61F 2002/07; A61F 2002/30112
USPC ................................................ 623/1.38–1.48
See application file for complete search history.

(56) References Cited

U.S. PATENT DOCUMENTS 3,867,190 A   2/1975   Schmitt et al.
5,298,276 A   3/1994   Jayaraman
(Continued)

FOREIGN PATENT DOCUMENTS

CN   1328853 A   1/2002
CN   1569270 A   1/2005
(Continued)

OTHER PUBLICATIONS

Bae, et al. Drug delivery. Fundamentals and methods of tissue engineering. From 'Frontiers in Tissue Engineering' edited by Patrick et al. Feb. 20, 1998; Ch II.14:263-272.
(Continued)

*Primary Examiner* — Alvin Stewart
(74) *Attorney, Agent, or Firm* — Wilson Sonsini Goodrich & Rosati

(57) ABSTRACT

A biodegradable stent prosthesis formed from a degradable material, having a plurality of luminal, abluminal, and side surface regions, wherein a surface portion extending between the abluminal and luminal surface region of at least some structural elements is convex or bulbous and optionally, where at least some of the abluminal surface regions may be concave.

38 Claims, 7 Drawing Sheets

(51) Int. Cl.
  *A61L 31/06* (2006.01)
  *A61L 31/14* (2006.01)
  *A61L 31/18* (2006.01)
  *A61F 2/958* (2013.01)
  *A61F 2/89* (2013.01)

(52) U.S. Cl.
  CPC .............. *A61F 2/89* (2013.01); *A61F 2/958* (2013.01); *A61F 2002/9155* (2013.01); *A61F 2002/91533* (2013.01); *A61F 2002/91558* (2013.01); *A61F 2002/91575* (2013.01); *A61F 2210/0004* (2013.01); *A61F 2210/0014* (2013.01); *A61F 2210/0071* (2013.01); *A61F 2230/001* (2013.01); *A61F 2240/001* (2013.01); *A61F 2250/0059* (2013.01); *A61F 2250/0067* (2013.01)

(56) References Cited

U.S. PATENT DOCUMENTS

| | | | |
|---|---|---|---|
| 5,441,483 A | 8/1995 | Avitall | |
| 5,447,724 A | 9/1995 | Helmus et al. | |
| 5,449,384 A | 9/1995 | Johnson | |
| 5,500,013 A | 3/1996 | Buscemi et al. | |
| 5,607,466 A | 3/1997 | Imbert et al. | |
| 5,670,161 A | 9/1997 | Healy et al. | |
| 5,674,286 A | 10/1997 | D'Alessio et al. | |
| 5,741,329 A | 4/1998 | Agrawal et al. | |
| 5,902,333 A | 5/1999 | Roberts et al. | |
| 5,935,119 A | 8/1999 | Guy et al. | |
| 5,957,975 A | 9/1999 | Lafont et al. | |
| 5,964,798 A | 10/1999 | Imran | |
| 5,980,564 A | 11/1999 | Stinson | |
| 6,027,526 A | 2/2000 | Limon et al. | |
| 6,039,755 A | 3/2000 | Edwin et al. | |
| 6,120,847 A | 9/2000 | Yang et al. | |
| 6,190,405 B1 | 2/2001 | Culombo et al. | |
| 6,224,803 B1 | 5/2001 | Tiernan | |
| 6,245,103 B1 | 6/2001 | Stinson | |
| 6,251,134 B1 | 6/2001 | Alt et al. | |
| 6,322,847 B1 | 11/2001 | Zhong et al. | |
| 6,323,256 B1 | 11/2001 | DelMain | |
| 6,395,326 B1 | 5/2002 | Castro et al. | |
| 6,537,312 B2 | 3/2003 | Datta et al. | |
| 6,547,814 B2 | 4/2003 | Edwin et al. | |
| 6,585,755 B2 | 7/2003 | Jackson et al. | |
| 6,626,939 B1 | 9/2003 | Burnside et al. | |
| 6,652,582 B1 | 11/2003 | Stinson | |
| 6,719,934 B2 | 4/2004 | Stinson | |
| 6,726,701 B2 | 4/2004 | Gilson et al. | |
| 6,761,784 B1 | 7/2004 | Hage | |
| 6,773,455 B2 | 8/2004 | Allen et al. | |
| 6,774,278 B1 | 8/2004 | Ragheb et al. | |
| 6,776,796 B2 | 8/2004 | Falotico et al. | |
| 6,805,898 B1 | 10/2004 | Wu et al. | |
| 6,863,757 B1 | 3/2005 | Gonzalez et al. | |
| 6,896,695 B2 | 5/2005 | Mueller et al. | |
| 6,920,677 B2 | 7/2005 | Dolan et al. | |
| 6,997,948 B2 | 2/2006 | Stinson | |
| 7,001,421 B2 | 2/2006 | Cheng et al. | |
| 7,108,716 B2 | 9/2006 | Burnside et al. | |
| 7,153,322 B2 | 12/2006 | Alt | |
| 7,258,697 B1 | 8/2007 | Cox et al. | |
| 7,279,005 B2 | 10/2007 | Stinson | |
| 7,285,304 B1 | 10/2007 | Hossainy et al. | |
| 7,291,166 B2 | 11/2007 | Cheng et al. | |
| 7,329,366 B1 | 2/2008 | Gale et al. | |
| 7,354,450 B2 | 4/2008 | Bicek et al. | |
| 7,377,939 B2 | 5/2008 | Williams et al. | |
| 7,390,333 B2 | 6/2008 | Dutta | |
| 7,550,005 B2 | 6/2009 | Bates et al. | |
| 7,563,277 B2 | 7/2009 | Case et al. | |
| 7,572,287 B2 | 8/2009 | Stinson | |
| 7,594,928 B2 | 9/2009 | Headley et al. | |
| 7,618,448 B2 | 11/2009 | Schmitz et al. | |
| 7,622,070 B2 | 11/2009 | Atladottir et al. | |
| 7,666,342 B2 | 2/2010 | Limon et al. | |
| 7,731,890 B2 | 6/2010 | Gale et al. | |
| 7,758,636 B2 | 7/2010 | Shanley et al. | |
| 7,824,601 B1 | 11/2010 | Stankus et al. | |
| 7,829,008 B2 | 11/2010 | Gueriguian et al. | |
| 7,875,233 B2 | 1/2011 | Huang et al. | |
| 7,964,136 B2 | 6/2011 | Sabaria | |
| 7,967,998 B2 | 6/2011 | Gale et al. | |
| 7,971,333 B2 | 7/2011 | Gale et al. | |
| 8,043,553 B1 | 10/2011 | Durcan | |
| 8,057,534 B2 | 11/2011 | Boismier et al. | |
| 8,062,465 B1 | 11/2011 | Huang et al. | |
| 8,172,897 B2 | 5/2012 | Gale et al. | |
| 8,173,062 B1 | 5/2012 | Durcan | |
| 8,182,890 B2 | 5/2012 | Zheng et al. | |
| 8,241,554 B1 | 8/2012 | Abbate et al. | |
| 8,268,228 B2 | 9/2012 | Huang et al. | |
| 8,323,760 B2 | 12/2012 | Zheng et al. | |
| 8,425,587 B2 | 4/2013 | Trollsas et al. | |
| 8,501,079 B2 | 8/2013 | Glauser et al. | |
| 8,545,546 B2 | 10/2013 | Wang | |
| 8,562,670 B2 | 10/2013 | Pacetti et al. | |
| 8,636,792 B2 | 1/2014 | Zheng et al. | |
| 8,709,071 B1 | 4/2014 | Huang et al. | |
| 8,740,839 B2 | 6/2014 | Eaton et al. | |
| 8,778,256 B1 | 7/2014 | Huang et al. | |
| 8,795,030 B2 | 8/2014 | Huang et al. | |
| 8,814,930 B2 | 8/2014 | Zheng et al. | |
| 8,834,556 B2 | 9/2014 | Papp et al. | |
| 8,840,660 B2 | 9/2014 | Weber | |
| 8,852,263 B2 | 10/2014 | Wang | |
| 8,872,062 B2 | 10/2014 | Chen et al. | |
| 8,900,292 B2 | 12/2014 | Gregorich et al. | |
| 8,956,403 B2 | 2/2015 | Gregorich et al. | |
| 9,005,276 B2 | 4/2015 | Fox et al. | |
| 9,119,905 B2* | 9/2015 | Zheng | A61F 2/82 |
| 9,259,339 B1* | 2/2016 | Yan | A61L 31/06 |
| 2001/0016729 A1 | 8/2001 | Divino et al. | |
| 2001/0016769 A1 | 8/2001 | Hojeibane | |
| 2001/0016770 A1 | 8/2001 | Allen et al. | |
| 2001/0021871 A1 | 9/2001 | Stinson | |
| 2001/0053929 A1 | 12/2001 | Vonesh et al. | |
| 2002/0007209 A1 | 1/2002 | Scheerder et al. | |
| 2002/0038146 A1 | 3/2002 | Harry | |
| 2002/0161430 A1 | 10/2002 | Jang | |
| 2002/0165597 A1 | 11/2002 | Clerc et al. | |
| 2002/0183581 A1 | 12/2002 | Yoe et al. | |
| 2002/0193336 A1 | 12/2002 | Elkins et al. | |
| 2003/0004563 A1 | 1/2003 | Jackson et al. | |
| 2003/0033007 A1 | 2/2003 | Sirhan et al. | |
| 2003/0050692 A1 | 3/2003 | Sirhan et al. | |
| 2003/0064097 A1 | 4/2003 | Patel et al. | |
| 2003/0083732 A1 | 5/2003 | Stinson | |
| 2003/0088307 A1 | 5/2003 | Shulze et al. | |
| 2003/0093143 A1 | 5/2003 | Zhao et al. | |
| 2003/0144726 A1 | 7/2003 | Majercak et al. | |
| 2003/0144729 A1 | 7/2003 | Bicek et al. | |
| 2003/0199993 A1 | 10/2003 | Gellman et al. | |
| 2003/0236320 A1 | 12/2003 | Martin et al. | |
| 2004/0006382 A1 | 1/2004 | Sohier | |
| 2004/0073290 A1 | 4/2004 | Chouinard | |
| 2004/0199242 A1 | 10/2004 | Hong et al. | |
| 2005/0031704 A1 | 2/2005 | Ahn | |
| 2005/0060020 A1 | 3/2005 | Jenson | |
| 2005/0070991 A1 | 3/2005 | Pienknagura | |
| 2005/0070996 A1 | 3/2005 | Dinh et al. | |
| 2005/0075625 A1 | 4/2005 | Dao et al. | |
| 2005/0075716 A1 | 4/2005 | Yan | |
| 2005/0123588 A1 | 6/2005 | Zhu et al. | |
| 2005/0125051 A1 | 6/2005 | Eidenschink et al. | |
| 2005/0171595 A1 | 8/2005 | Feldman et al. | |
| 2005/0187615 A1 | 8/2005 | Williams et al. | |
| 2005/0209680 A1 | 9/2005 | Gale et al. | |
| 2005/0216074 A1 | 9/2005 | Sahatjian et al. | |
| 2005/0232964 A1 | 10/2005 | Fennimore, Jr. et al. | |
| 2006/0025852 A1 | 2/2006 | Armstrong et al. | |
| 2006/0076708 A1 | 4/2006 | Huang et al. | |

(56) References Cited

U.S. PATENT DOCUMENTS

| | | |
|---|---|---|
| 2006/0100695 A1 | 5/2006 | Peacock et al. |
| 2006/0111485 A1 | 5/2006 | Laghi |
| 2006/0122697 A1 | 6/2006 | Shanley et al. |
| 2006/0129222 A1 | 6/2006 | Stinson |
| 2006/0136048 A1 | 6/2006 | Pacetti et al. |
| 2006/0147538 A1 | 7/2006 | Craig et al. |
| 2006/0229711 A1 | 10/2006 | Yan et al. |
| 2006/0251618 A1 | 11/2006 | Dennis et al. |
| 2006/0265048 A1 | 11/2006 | Cheng et al. |
| 2006/0271170 A1 | 11/2006 | Gale et al. |
| 2006/0287710 A1 | 12/2006 | Lendlein et al. |
| 2007/0023974 A1 | 2/2007 | Wu |
| 2007/0231365 A1 | 10/2007 | Wang et al. |
| 2007/0253999 A1 | 11/2007 | Huang et al. |
| 2007/0259099 A1 | 11/2007 | Van |
| 2007/0270941 A1 | 11/2007 | Headley et al. |
| 2007/0271763 A1 | 11/2007 | Huang et al. |
| 2007/0278720 A1 | 12/2007 | Wang et al. |
| 2007/0281117 A1 | 12/2007 | Kaplan et al. |
| 2007/0282426 A1 | 12/2007 | Wang et al. |
| 2007/0282434 A1 | 12/2007 | Wang et al. |
| 2007/0283552 A1 | 12/2007 | Gale et al. |
| 2007/0290412 A1 | 12/2007 | Capek et al. |
| 2007/0299505 A1 | 12/2007 | Gregorich et al. |
| 2008/0051866 A1 | 2/2008 | Chen et al. |
| 2008/0081063 A1 | 4/2008 | Wang et al. |
| 2008/0082162 A1 | 4/2008 | Boismier et al. |
| 2008/0097571 A1 | 4/2008 | Denison et al. |
| 2008/0097580 A1 | 4/2008 | Dave |
| 2008/0103584 A1 | 5/2008 | Su et al. |
| 2008/0147165 A1 | 6/2008 | Hossainy et al. |
| 2008/0177373 A1 | 7/2008 | Huang et al. |
| 2008/0177374 A1 | 7/2008 | Zheng et al. |
| 2008/0243243 A1 | 10/2008 | Williams et al. |
| 2008/0249608 A1 | 10/2008 | Dave |
| 2008/0306579 A1 | 12/2008 | Dolan et al. |
| 2009/0030507 A1 | 1/2009 | Klocke et al. |
| 2009/0095715 A1 | 4/2009 | Sabaria |
| 2009/0096137 A1 | 4/2009 | Williams et al. |
| 2009/0099639 A1 | 4/2009 | Sabaria |
| 2009/0105800 A1 | 4/2009 | Sabaria |
| 2009/0146348 A1 | 6/2009 | Huang et al. |
| 2009/0208555 A1 | 8/2009 | Kuttler et al. |
| 2009/0216309 A1 | 8/2009 | Granada et al. |
| 2009/0228094 A1 | 9/2009 | Yan et al. |
| 2010/0036478 A1 | 2/2010 | Wang et al. |
| 2010/0038822 A1 | 2/2010 | Wang et al. |
| 2010/0049300 A1 | 2/2010 | Harder |
| 2010/0198331 A1 | 8/2010 | Rapoza et al. |
| 2010/0217370 A1 | 8/2010 | Scheuermann et al. |
| 2010/0244329 A1 | 9/2010 | Hossainy et al. |
| 2010/0252965 A1 | 10/2010 | Wang et al. |
| 2010/0262224 A1 | 10/2010 | Kleiner |
| 2010/0292773 A1 | 11/2010 | Schmid et al. |
| 2011/0022163 A1 | 1/2011 | Wang et al. |
| 2011/0054591 A1 | 3/2011 | Sahatjian et al. |
| 2011/0062638 A1 | 3/2011 | Glauser et al. |
| 2011/0160757 A1 | 6/2011 | Ferrera et al. |
| 2011/0215505 A1 | 9/2011 | Kleiner et al. |
| 2011/0238158 A1 | 9/2011 | Heringes et al. |
| 2011/0238162 A1 | 9/2011 | Busold et al. |
| 2011/0260352 A1 | 10/2011 | Tang et al. |
| 2011/0260358 A1 | 10/2011 | Wang et al. |
| 2012/0071962 A1 | 3/2012 | Huang et al. |
| 2012/0187606 A1 | 7/2012 | Zheng et al. |
| 2012/0226345 A1 | 9/2012 | Zheng et al. |
| 2012/0271396 A1 | 10/2012 | Zheng et al. |
| 2012/0290070 A1 | 11/2012 | Wang et al. |
| 2012/0290071 A1 | 11/2012 | Wang et al. |
| 2013/0084322 A1 | 4/2013 | Wu |
| 2013/0085564 A1 | 4/2013 | Papp et al. |
| 2013/0150943 A1 | 6/2013 | Zheng et al. |
| 2013/0190676 A1 | 7/2013 | Dickinson et al. |
| 2013/0331927 A1 | 12/2013 | Zheng et al. |
| 2014/0004312 A1 | 1/2014 | Foreman et al. |
| 2014/0012362 A1 | 1/2014 | Gale et al. |
| 2014/0018903 A1 | 1/2014 | Eli et al. |
| 2014/0025161 A1 | 1/2014 | Stankus et al. |
| 2014/0121294 A1 | 5/2014 | Huang et al. |
| 2014/0188243 A1 | 7/2014 | Zheng et al. |
| 2014/0252683 A1 | 9/2014 | Huang et al. |
| 2014/0277373 A1 | 9/2014 | Huang et al. |
| 2014/0350659 A1 | 11/2014 | Zheng et al. |
| 2015/0025619 A1 | 1/2015 | Zheng et al. |
| 2015/0073536 A1 | 3/2015 | Rapoza et al. |
| 2015/0320577 A1 | 11/2015 | Zheng et al. |
| 2015/0374521 A1 | 12/2015 | Zheng et al. |
| 2016/0045344 A1 | 2/2016 | Yan et al. |

FOREIGN PATENT DOCUMENTS

| | | |
|---|---|---|
| JP | H11512626 A | 11/1999 |
| JP | 2000202032 A | 7/2000 |
| JP | 2003500101 A | 1/2003 |
| JP | 2004149692 A | 5/2004 |
| JP | 2005298617 A | 10/2005 |
| JP | 2006192111 A | 7/2006 |
| JP | 2006223860 A | 8/2006 |
| JP | 2011502195 A | 1/2011 |
| WO | WO-9204393 A1 | 3/1992 |
| WO | WO-0195834 A1 | 12/2001 |
| WO | WO-02091956 A1 | 11/2002 |
| WO | WO-03034940 A2 | 5/2003 |
| WO | WO-2004052420 A2 | 6/2004 |
| WO | WO-2004080332 A2 | 9/2004 |
| WO | WO-2004110315 A1 | 12/2004 |
| WO | WO-2004110515 A1 | 12/2004 |
| WO | WO-2004080332 A3 | 4/2005 |
| WO | WO-2005096992 A1 | 10/2005 |
| WO | WO-2005115277 A2 | 12/2005 |
| WO | WO-2005115277 A3 | 5/2007 |
| WO | WO-2007126599 A2 | 11/2007 |
| WO | WO-2007146354 A2 | 12/2007 |
| WO | WO-2008002479 A2 | 1/2008 |
| WO | WO-2008002636 A2 | 1/2008 |
| WO | WO-2008005390 A1 | 1/2008 |
| WO | WO-2008008416 A1 | 1/2008 |
| WO | WO-2008011048 A2 | 1/2008 |
| WO | WO-2007146354 A3 | 2/2008 |
| WO | WO-2008016667 A2 | 2/2008 |
| WO | WO-2008016696 A2 | 2/2008 |
| WO | WO-2008016696 A3 | 3/2008 |
| WO | WO-2008033263 A2 | 3/2008 |
| WO | WO-2008002636 A3 | 4/2008 |
| WO | WO-2008051867 A2 | 5/2008 |
| WO | WO-2007126599 A3 | 7/2008 |
| WO | WO-2008089434 A2 | 7/2008 |
| WO | WO-2008051867 A3 | 8/2008 |
| WO | WO-2008098434 A1 | 8/2008 |
| WO | WO-2008002479 A3 | 9/2008 |
| WO | WO-2008016667 A3 | 11/2008 |
| WO | WO-2008137821 A1 | 11/2008 |
| WO | WO-2008011048 A3 | 3/2009 |
| WO | WO-2008033263 A3 | 4/2009 |
| WO | WO-2011025945 A1 | 3/2011 |
| WO | WO-2014091438 A2 | 6/2014 |

OTHER PUBLICATIONS

Breiby, et al. Quantification of preferential orientation in conjugated polymers using X-ray diffraction. J. Polymer Science Part B: Polymer Physics. 2003; 41(20):2375-2393.

Cruz, et al. Quantitative mapping of the orientation of fibroin beta-sheets in *B. mori* cocoon fibers by scanning transmission X-ray microscopy. Biomacromolecules. Mar. 2006;7(3):836-43.

Donald, et al. Electron Microscopy of Banded Structures in Oriented Thermotropic Polymers. J. Materials Science. 1983; 18:1143-1150.

Fuhrman, et al. Central nervous system. From 'Tissue Engineering: From Lab to Clinic' edited by Pallua et al. 2010; Ch12:221-244.

Hacker, et al. Synthetic polymers. From 'Principles of Regenerative Medicine 2nd ed.' Edited by Atala et al. 2011; Ch 33:587-622.

(56) References Cited

OTHER PUBLICATIONS

Hara. Ion-containing polymers and their biological interactions. Polyelectrolytes Science and Technology. 1993; Ch 6:321-325.
Hombreiro-Perez, et al. Non-degradable microparticles containing a hydrophilic and/or a lipophilic drug: preparation, characterization and drug release modeling. J Control Release. Mar. 26, 2003;88(3):413-28.
Lamberti, et al. Real-time orientation and crystallinity measurements during the isotactic polypropylene film-casting process. J. Polymer Science Part B: Polymer Physics. 2003; 41(9):998-1008.
Lee, et al. Retardation of enzymatic degradation of microbial polyesters using surface chemistry: effect of addition of non-degradable polymers. Surface Science. 2003; 542(3):235-243.
Ma, et al. Scaffolding in Tissue Engineering. 2005; pp. 78-80.
Majoros, et al. Poly(amidoamine) dendrimer synthesis and characterization. Dendrimer-based Nanomedicine. 2008; Ch 3:35-57.
Qin, et al. Synthesis and Characterization of Unsaturated Thermotropic Polyesters Prepared via Acyclic Diene Metathesis Polymerization. Macromolecules. 2004; 37:5239-5249.
Sanders. Controlled delivery systems for peptides. From 'Peptide and protein drug delivery' Edited by Vincent Lee, Advances in Parenteral science vol. 4. 1990; Ch 19:785-806.
Seal, et al. Polymeric biomaterials for tissue and organ regeneration. Materials Science and Engineering. R34. 2001; 147-230.
Shastri. Non-degradable biocompatible polymers in medicine: past, present, and future. Current Pharmaceutical Biotechnology. 2003; 4:331-337.
Tanimoto, et al. Comparison of in vivo acute stent recoil between the bioabsorbable everolimus-eluting coronary stent and the everolimus-eluting cobalt chromium coronary stent: insights from the Absorb and Spirit trials. Catheter Cardiovasc Interv. Oct. 1, 2007;70(4):515-23.
Valimaa, et al. Viscoelastic memory and self-expansion of self-reinforced bioabsorbable stents. Biomaterials. Sep. 2002; 23(17):3575-82.
Weir, et al. Processing, Annealing and Sterilisation of Poly-L-Lactide. Biomaterials. 2004; 25: 3939-3949.
Co-pending U.S. Appl. No. 14/604,621, filed Jan. 23, 2015.
Co-pending U.S. Appl. No. 15/043,331, filed Feb. 12, 2016.
European search report and search opinion dated Feb. 18, 2015 for EP Application No. 12804895.6.
European search report and search opinion dated Dec. 20, 2012 for Application No. 8727927.9.
"International search report and written opinion dated Apr. 13, 2015 for PCT Application No. PCT/US15/12780".
International search report and written opinion dated Aug. 1, 2008 for PCT/US2008/051479.
International search report and written opinion dated Aug. 1, 2008 for PCT/US2008/051497.
International search report and written opinion dated Sep. 25, 2012 for PCT/US2012/44736.
Notice of allowance dated May 12, 2014 for U.S. Appl. No. 13/897,302.
Notice of allowance dated Jul. 15, 2015 for U.S. Appl. No. 14/461,159.
Notice of allowance dated Dec. 13, 2013 for U.S. Appl. No. 13/539,770.
Notice of allowance dated Dec. 23, 2015 for U.S. Appl. No. 14/682,014.
Office action dated Mar. 2, 2010 for U.S. Appl. No. 12/016,077.
Office action dated Mar. 10, 2016 for U.S. Appl. No. 14/611,043.
Office action dated Mar. 30, 2011 for U.S. Appl. No. 12/016,085.
Office action dated Apr. 1, 2011 for U.S. Appl. No. 12/016,077.
Office action dated Apr. 24, 2015 for U.S. Appl. No. 14/461,159.
Office action dated Jul. 2, 2013 for U.S. Appl. No. 12/016,077.
Office action dated Jul. 12, 2012 for U.S. Appl. No. 13/473,354.
Office action dated Jul. 15, 2015 for U.S. Appl. No. 14/682,014.
Office action dated Jul. 17, 2013 for U.S. Appl. No. 13/539,770.
Office action dated Aug. 1, 2014 for U.S. Appl. No. 14/097,087.
Office action dated Oct. 27, 2011 for U.S. Appl. No. 12/016,077.
Office action dated Nov. 10, 2010 for U.S. Appl. No. 12/016,077.
Office action dated Nov. 14, 2014 for U.S. Appl. No. 14/461,159.
Office action dated Dec. 5, 2012 for U.S. Appl. No. 12/016,077.
Office action dated Dec. 15, 2011 for U.S. Appl. No. 12/016,085.
Office action dated Dec. 18, 2013 for U.S. Appl. No. 13/897,302.
Office action dated Oct. 4, 2012 for U.S. Appl. No. 13/539,770.

\* cited by examiner

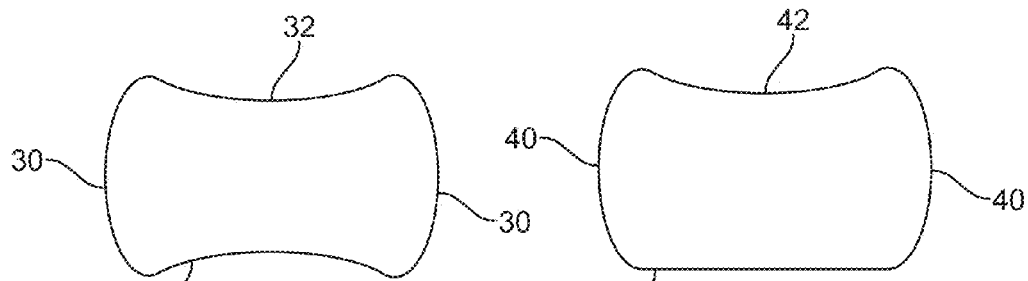
FIG. 3
FIG. 4
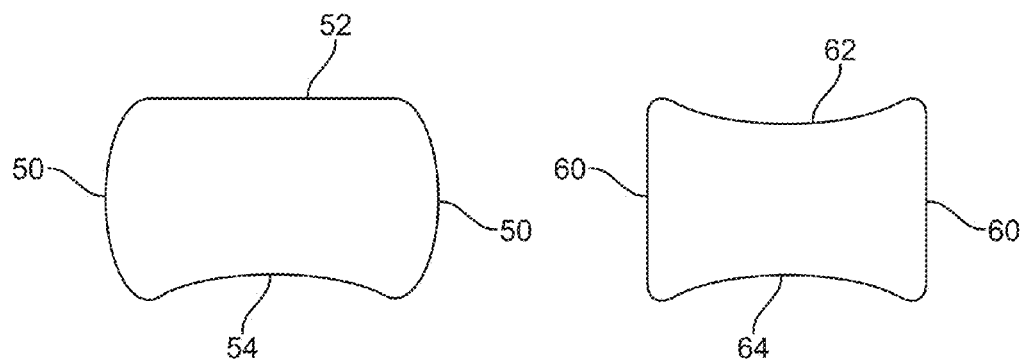
FIG. 5
FIG. 6
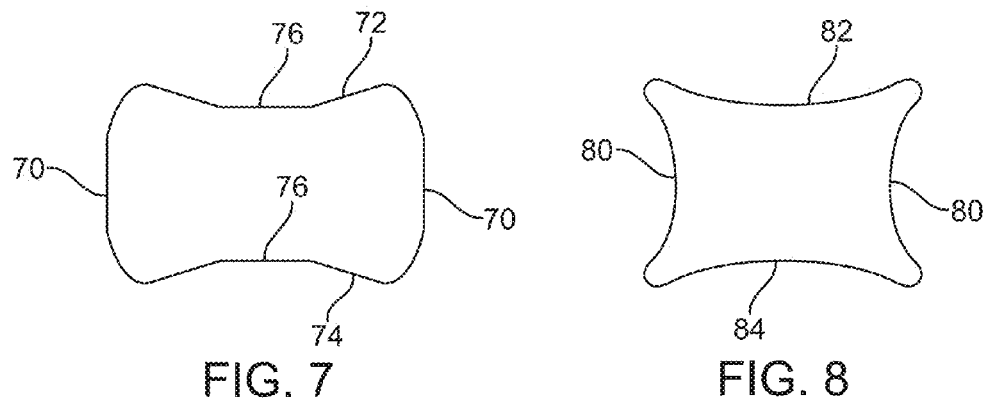
FIG. 7
FIG. 8
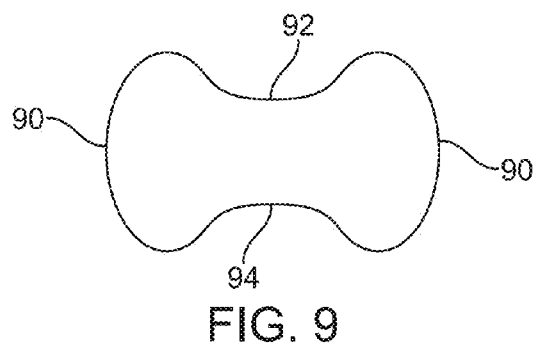
FIG. 9

BIODEGRADABLE ENDOPROSTHESES AND METHODS OF THEIR FABRICATION

CROSS-REFERENCE TO RELATED APPLICATIONS

This application is a continuation-in-part of U.S. patent application Ser. No. 14/682,014, filed Apr. 8, 2015, which is a continuation-in-part of U.S. patent application Ser. No. 14/461,159, filed Aug. 15, 2014, both of which are incorporated herein by reference.

FIELD OF THE INVENTION

The present invention relates generally to medical devices and methods for their fabrication. In particular, the present invention relates to the fabrication of biodegradable endoprostheses, such as stent prostheses, having shaped surface regions for enhanced implantation performance, enhanced drug delivery or other enhanced properties.

Stents are generally tubular-shaped devices which function to hold open or reinforce a segment of a blood vessel or body lumen, such as a coronary artery, carotid artery, saphenous vein graft, or femoral artery. They also are suitable to support and hold back a dissected arterial lining that could otherwise occlude the body lumen, to stabilize plaque, or to support/hold open a bioprosthetic valves. Stents can be formed from various materials, particularly polymeric and/or metallic materials, and may be non-degradable or biodegradable. Stents are typically delivered to the target area within the body lumen using a catheter. With balloon-expandable stents, the stent is mounted onto a balloon catheter, navigated to the appropriate area, and the stent is expanded by inflating the balloon. A self-expanding stent is delivered to the target area and released, expanding to treat the disease.

Of particular interest to the present invention are biodegradable stents, including polymer stents, such as biodegradable polymer stents or also called scaffolds and other endoprostheses. Biodegradable scaffolds are usually formed from polymers which degrade by various mechanisms such as by hydrolysis and other reaction mechanisms in the vascular or other body environment. This invention also applies to metallic biodegradable stents.

Biodegradable polymer implantable devices and methods of making them are also described in commonly owned U.S. Pat. Nos. 8,182,890; 8,323,760; 8,636,792; 8,814,930; and U.S. Patent Publication Nos. 2008/0177373 and 2006/0029711 the entire disclosure of each of which is incorporated herein by reference.

BRIEF SUMMARY OF THE INVENTION

In embodiments of the disclosure an expandable biodegradable stent prosthesis comprises: a tubular expandable stent prosthesis body comprising a biodegradable material, for example a polymeric biodegradable material, said expandable stent prosthesis body comprising stent structural elements each having a luminal surface and an abluminal surface and a thickness between said luminal and abluminal surfaces; wherein a region extending between the abluminal surface and the luminal surface of at least some structural elements is bulbous.

In other embodiments two side surface regions extending between the luminal and abluminal surface regions of at least some stent structural elements are bulbous.

In embodiments of the disclosure an expandable biodegradable stent prosthesis comprises: an expandable stent prosthesis body comprising a biodegradable polymeric material, wherein the stent comprises a plurality of stent structural elements, wherein said stent structural elements each have a luminal surface region, an abluminal surface region, and two side surface regions extending between the luminal and abluminal surface regions; and wherein at least some of the stent structural elements have a bulbous shape coupling said abluminal and said luminal surface regions to form a dogbone shaped cross section.

In embodiments of the disclosure an expandable biodegradable stent prosthesis comprises: a tubular expandable stent prosthesis body comprising a biodegradable polymeric material, said expandable stent prosthesis body comprising stent structural elements each having a luminal surface and an abluminal surface and a thickness between said luminal and abluminal surfaces; wherein the thickness varies across the width of at least some of the structural elements.

In embodiments of the disclosure an expandable biodegradable stent prosthesis comprises a tubular expandable stent prosthesis body formed from a biodegradable, for example polymeric, material, said expandable stent prosthesis body comprising stent structural elements having luminal and abluminal surface regions; wherein at least some of the body abluminal surface regions are concave or flat across substantially their width. Said stent prosthesis may be expandable from a crimped configuration to an expanded larger configuration to support a blood vessel. At least some or substantially all of the side surface regions may be substantially convex. At least some or substantially all of the side surface regions which in use face the distal end of the delivery catheter may be substantially convex or completely convex.

The stent structural elements may for example comprise struts and crowns. The struts and crowns may each have an abluminal surface region and a luminal surface region. The stent structural elements may comprise struts, crowns, and links, each having an abluminal surface region and a luminal surface region. Each strut, crown, and link may have an abluminal surface region, a luminal surface region, and two side surface regions extending between the abluminal and luminal surface regions.

The expandable stent prosthesis body may comprise expandable serpentine rings, each ring may be composed of struts joined by crowns, and each ring may be connected to an adjacent ring by at least one link.

The struts and crowns may have two side surface regions extending between the luminal and abluminal surface regions, wherein at least some of the side surface regions are convex.

The expandable prosthesis may be formed of a biodegradable polymeric material which comprises at least two biodegradable polymers.

The expandable prosthesis body may have been treated to form the concave abluminal surface regions.

In embodiments of the disclosure an expandable biodegradable stent prosthesis comprises a tubular expandable stent prosthesis body comprising a biodegradable, for example polymeric material, said expandable stent prosthesis body comprising stent structural elements having luminal and abluminal surface regions; wherein at least some of the side surface regions are convex across substantially the thickness of said side surface regions. Said stent prosthesis may be expandable from a crimped configuration to an expanded larger configuration to support a blood vessel. Substantially all of the side surface region may be convex.

At least some or substantially all of the side surface regions which in use face the distal end of the delivery catheter may be convex. At least some or substantially all of the abluminal surface regions may be concave, flat or straight, substantially across their width.

The convex side surface regions and concave, flat or straight abluminal surface regions may be prepared by treating to shape the stent structural elements or may be formed to have the desired shapes. The treatment may comprise shaping by application of a solvent by at least one of dipping, spraying, or contact with a solvent vapor. The treatment may alternatively or additionally comprise shaping by at least one of tumbling, agitating, deburring, scraping, media blasting, laser treatment and heat treatment.

The treatment may not significantly dissolve (or permanently remove) the polymeric material from which said prosthesis is formed. For example, the treatment may shift material from one stent structural element (also referred to herein as a scaffold structure) to an adjacent surface region of the same or different stent structural element without a substantial change in body weight or mass of said expandable stent prosthesis. The application of the solvent may soften the polymeric material allowing it to move, flow or redistribute from one surface region to another surface region on the stent structural elements without the polymeric material becoming dissolved in (or otherwise dispersed in) in the solvent.

The expandable stent prosthesis body may have been patterned from a tube by a laser. The expandable stent may have been patterned from a substantially continuous tubular body, substantially free from discontinuities or substantially free from holes.

The expandable stent prosthesis body may have been patterned from a tube by a laser and the stent structural elements treated to form the concave abluminal surface regions and convex side surface regions.

A coating comprising at least one drug may be formed over at least some portions of the expandable stent prosthesis body.

The stent prosthesis may further comprise a coating over the expandable stent prosthesis body with the coating such that concave surface regions of said stent structural elements remain substantially concave and convex surface regions of said stent structural elements remain substantially convex. Whatever shape the surface has may remain substantially the same shape after the coating.

A weight or mass of the expandable stent prosthesis after treatment may be substantially the same as before treatment.

The biodegradable polymeric material may have an elastic modulus of at least 0.35 GPa.

The biodegradable polymeric material may comprise one or more of polymers and copolymers.

The prosthesis may be capable of being expanded from a crimped diameter to a deployed diameter at body temperature without fracture.

The prosthesis may be capable of being expanded from a crimped diameter to a deployed diameter at body temperature without substantial rotation of at least one of the stent structural elements about their axis.

The biodegradable polymeric material may comprise at least one material selected from the group consisting of lactides, poly-DL-Lactide, polylactide-co-glycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

The prosthesis may be balloon expandable.

The biodegradable polymeric material may have a molecular weight from 100 KDa to 1000 Kda.

The body may have been treated to adjust a thickness of at least one of the stent structural elements from a first thickness before treatment to a second thickness after treatment, wherein the second thickness is greater than the first thickness and the second thickness may vary across the width of the stent structural element.

The body may have been treated to cause a thickness of a plurality of stent structural elements between the luminal and abluminal surface regions to increase while a width of the stent structural elements between the side surface regions remains substantially the same.

The body may be treated by exposing the expandable prosthesis to a solvent for a predetermined period of time to provide at least some substantially convex side surface regions and at least some concave abluminal surface regions of said stent structural elements.

The body may have been treated to cause a thickness of the plurality of stent structural elements between the luminal and abluminal surface regions to increase while decreasing a minimum width of the stent structural elements between the side surface regions by redistributing the polymeric material.

In an embodiment, a stent prosthesis comprises a tubular expandable stent prosthesis body formed from a biodegradable material, such as a polymeric material, said material is patterned into a stent radially expandable from a crimped diameter to a deployed larger configuration, wherein the stent comprises a plurality of stent structural elements, such as struts joined by crowns, wherein said stent structural elements each have a luminal surface region, an abluminal surface region, and two side surface regions extending between the luminal and abluminal surface regions; and wherein at least some of the side surface regions have a convex shape across substantially the thickness of said side surface regions; said stent prosthesis in the deployed diameter has sufficient strength to support a blood vessel. The stent may comprise a plurality of stent structural elements such as struts joined by crowns where at least some of the crowns are connected to adjacent crowns by links or where at least some of the crowns are connected to adjacent crowns.

At least some of the stent structural element abluminal surface regions may have a concave shape across substantially their width. At least some of the stent structural element abluminal surface regions may have a surface shape similar to the surface of a dogbone, that is, a combination of convex and concave shapes across the width of the abluminal surface region.

Substantially all of the side surface regions may have a convex shape across substantially the thickness of said side surface regions.

The prosthesis may have been treated by contact with a solvent to redistribute said polymeric material to provide said concave or convex surface regions as the case may be.

The prosthesis may have been treated by contact with a solvent to flow said polymeric material to provide said concave or convex surface regions as the case may be.

In embodiments of the disclosure an expandable biodegradable stent prosthesis comprises a tubular expandable stent prosthesis body comprising a biodegradable metal or metal alloy, such as zinc, magnesium, and iron, and alloys thereof, wherein the stent is treated to modify at least some abluminal surface regions making them concave substantially across the width of said abluminal surface regions, and/or to modify at least some of side surface regions making them substantially convex across the thickness of said side surface regions. The above surface region modifications may be provided without a substantial change in weight or mass compared to before treatment, or without losing more than 15% in weight or mass after treatment, or without losing more than 25% in weight or mass after treatment. The metallic tubular body may be substantially continuous or substantially free from discontinuities or substantially free from holes before patterning.

The prosthesis may have been treated by contact with a solvent to redistribute said polymeric material to vary the thickness of at least one stent structural element and/or to vary the width of at least one stent structural element, for example to provide at least one stent structural element with a width that is larger away from than close to said abluminal and luminal surface regions and/or with a thickness that is smaller away from than close to the side surface regions.

In embodiments of the disclosure an expandable biodegradable stent prosthesis comprises a tubular expandable stent prosthesis body comprising a biodegradable polymeric material, wherein the tubular body has an initial diameter, which may be larger than an intended deployed diameter (labeled or nominal diameter) of the stent prosthesis (may be 1.1-1.5 times larger than intended deployed diameter). The tubular body may be patterned with a laser or by etching to provide stent structural elements, with the patterning preferably occurring at the initial diameter that is 1.1-1.5 times the intended deployed diameter. After patterning, some or all of the stent structural elements may be treated to provide a convex shape to at least some of the side surface regions and optionally a flat or concave shape to at least some of the abluminal surface regions. Said treatment may be performed at substantially the as-formed (initial) tubular diameter, The stent prosthesis may be treated by heating the polymeric material above Tg (the glass transition temperature) and below Tm (the melting point) of said polymeric material before or/and after the patterning of the stent prosthesis to provide or modify various physical properties of the resulting stent prosthesis. The stent structural elements may be heated to above Tg and below Tm of the polymeric material after said shaping treatment but before being crimped to a smaller diameter. The stent prosthesis is capable of being radially expanded or/and radially crimped and following insertion of the crimped prosthesis may be expanded to a deployed to a diameter larger than the crimped diameter to support a blood vessel or other body lumen without fracture.

In disclosed embodiments, a stent is formed from a substantially continuous body (or a body at least substantially free from holes and/or discontinuities), said body has been patterned into a stent body comprising stent structural elements each having at least two surface regions, said at least two surface regions are an abluminal surface region and a luminal surface region, wherein said stent structural elements have a thickness, wherein said thickness of at least some stent structural elements is variable across the width of said stent structural elements, wherein the thickness extends between the abluminal surface and luminal surface regions of a said stent structural element which may have a convex shape. In preferred embodiments, at least some structural elements have a larger thickness at about an end of their abluminal surface region than about a midpoint of their abluminal surface region. In other embodiments, the thickness at about an end of an abluminal region is smaller than that about a midpoint of the abluminal surface region. In preferred embodiments, the cross section of at least some stent structural elements is oval, or dogbone shape. In some embodiments, the maximum stent structural element thickness is at least 1.05 times the minimum stent structural element thickness. In other embodiments, the maximum stent structural element thickness ranges between 1.05-1.3 times the minimum stent structural element thickness.

In some embodiments, a stent is formed from a substantially continuous body (that is a body that is at least substantially free from holes and/or discontinuities), said body has been patterned into a stent body comprising stent structural elements each having at least two surface regions, said at least two surface regions are an abluminal surface region and a luminal surface region, wherein said structural elements have a thickness, wherein the surface area extending between the abluminal surface and luminal surface regions of the at least some stent structural elements is convex. In some embodiments, the abluminal surface region is substantially concave or substantially flat across the width of said stent structural element. In preferred embodiments, the cross section of at least some stent structural elements is oval or dogbone shape.

In a preferred embodiment, a degradable stent is formed from a substantially continuous body comprising a polymeric material, formed by extrusion, dipping, spraying, or molding, said body has been patterned after forming into a stent body comprising stent structural elements said structural elements comprising two surface regions, an abluminal surface region and a luminal surface region, wherein said structural elements have a thickness, wherein the region extending across the thickness between the abluminal surface and luminal surface regions of the at least some stent structural elements is bulbous in shape. The stent prosthesis may have a thickness that varies across the width of said structural elements. The stent prosthesis structural elements may have at least one side surface region wherein the side surface region is convex across substantially the thickness of said structural elements. The stent prosthesis abluminal surface region may have a concave shape across substantially the width of said structural elements, said abluminal surface may have a bulbous region about an end region or towards an end region of said structural element width, wherein said bulbous region may have a convex shape, wherein the bulbous region maximum thickness is greater than a minimum thickness across the width of said structural elements ranging from 3 micrometers to 100 micrometers, preferably 5 micrometers to 30 micrometers. The bulbous surface region coupling the abluminal and luminal surface regions may in some instances have a flat portion at about the middle of the bulbous or convex shape.

In another example wherein the stent prosthesis is treated to form the region having a bulbous shape, the bulbous region protrudes outwardly forming a convex shape.

A concave abluminal surface region minimizes or at least reduces the possibility of slippage of the scaffold when expanded to a deployed configuration, such that the structural elements hug the vessel wall or the plaque area better.

It can be appreciated that a prosthesis may have any or all of the features set out in this document.

BRIEF DESCRIPTION OF THE DRAWINGS

FIG. 3 is a cross section of a stent structural element having a concave abluminal surface region, a concave luminal surface region, and two convex side surface regions, showing a bulbous region extending between the luminal surface region and abluminal surface region;

FIG. 4 is a cross section of a stent structural element having convex side surface regions, a concave abluminal surface region and a substantially straight/flat luminal surface region, showing a bulbous region extending between the abluminal surface region and the luminal surface region;

FIG. 5 is a cross section of a stent structural element having two convex side surface regions, a substantially straight/flat abluminal surface region and a concave luminal surface region, showing a bulbous region extending between the abluminal surface region and the luminal surface region;

FIG. 6 is a cross section of a stent structural element having substantially straight side surface regions, a concave abluminal surface region and a concave luminal surface region, showing a bulbous region in the abluminal surface region extending or protruding outwardly and a bulbous region in the luminal surface region extending or protruding outwardly;

FIG. 7 is a cross section of a stent structural element having convex side surface regions, a concave abluminal surface region and a concave luminal surface region with a center part of the concave surface regions being substantially straight (flat), showing a bulbous region extending between the abluminal and luminal surface regions extending outwardly;

FIG. 8 is a cross section of a stent structural element having concave side surface regions, a concave abluminal surface region and a concave luminal surface region, showing bulbous regions in the abluminal surface region extending or protruding outwardly and bulbous regions in the luminal surface region extending or protruding outwardly;

FIG. 9 is a cross section of a stent structural element having a dogbone shape comprising concave luminal and abluminal surface regions, and convex side surface regions, showing a bulbous region extending between the abluminal surface region and the luminal surface region where the bulbous region comprises an abluminal surface region that has a convex shape towards the end of the structural element width and a luminal surface region that has a convex shape towards the end of the structural element width;

DETAILED DESCRIPTION OF THE INVENTION

Embodiments provide an expandable biodegradable stent prosthesis comprising: a tubular expandable stent prosthesis body comprising a biodegradable material, for example a polymeric biodegradable material, said expandable stent prosthesis body comprising stent structural elements each having a luminal surface and an abluminal surface and a thickness between said luminal and abluminal surfaces; wherein a region extending between the abluminal surface and the luminal surface of at least some structural elements is bulbous.

Embodiments provide an expandable biodegradable stent prosthesis comprising: a tubular expandable stent prosthesis body comprising a biodegradable material, for example a polymeric biodegradable material, said expandable stent prosthesis body comprising stent structural elements each having a surface with a luminal surface region, an abluminal surface region, coupling portions coupling the abluminal and luminal surface regions, and a thickness between said luminal and abluminal surface regions; wherein at least a part of at least some of the coupling portions is bulbous.

Embodiments provide an expandable biodegradable stent prosthesis comprising: a tubular expandable stent prosthesis body comprising a biodegradable material, for example a polymeric biodegradable material, said expandable stent prosthesis body comprising stent structural elements each having an interior, luminal, surface region and an exterior, abluminal, surface region such that when the stent prosthesis is placed in the lumen of a vessel, the luminal surface regions face the lumen of the vessel and the abluminal surface regions face the vessel wall; wherein at least some of the abluminal surface regions have a concave shape across substantially the width of said surface regions; and/or at least some of the luminal surface regions have a concave shape across substantially the width of said surface regions; and/or at least some of the side surface regions coupling the abluminal and luminal surface regions have a straight, convex or concave shape across substantially the width of said surface regions.

Each stent structural element (for example struts or other scaffold structure such as crowns or links) has a particular (certain) surface region geometry or is modified according to a treatment process described herein to provide that certain geometry. As an example, an expandable stent prosthesis may be formed by laser patterning or cutting from a tube or sheet of polymeric material to provide stent structural elements (for example struts or other scaffold structures such as crowns), with many having substantially rectangular or square cross sections and the expandable stent prosthesis may be treated to provide the certain geometry such as convex side surface regions and/or concave or flat abluminal surface regions.

Figure 1:
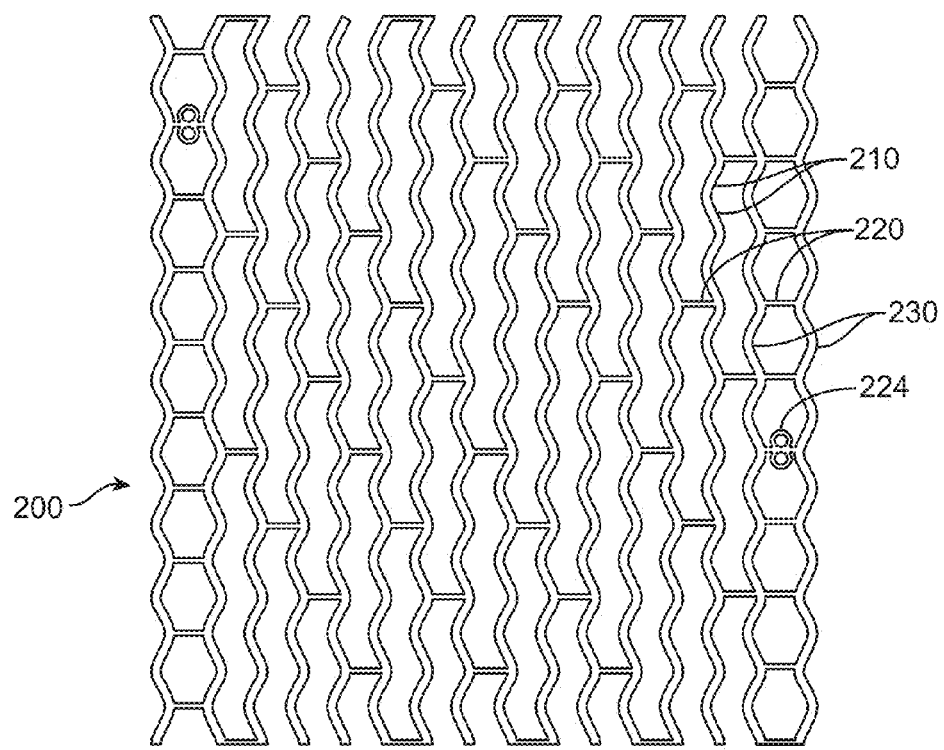
FIG. 1 depicts an example of a two dimensional stent pattern.

An exemplary scaffold pattern is shown in FIG. 1 represented in two dimensions. The scaffold body 200 comprises stent structural elements forming sinusoidal rings, in this example the stent structural elements comprise struts 210 and V or U shaped crowns 230 joining the struts. The rings are interconnected by links 220. In the example scaffold pattern shown, links 220 connect adjacent crowns. A length of the scaffold can be adjusted by changing a number of rings. Some of the links 220 or struts 210 may be replaced by or attached to one or more loops 224 each containing one, two or more radiopaque markers axially or radially or somewhere in between. For example two such pairs of radiopaque markers can be provided at the opposite ends of the scaffold, and/or at the opposite side of the scaffold. The scaffold 200 can be balloon expandable and has low recoil, has sufficient radial strength to support a body lumen, conformable to the body lumen, and has low percent shortening upon expansion of less than 15%. Many other scaffold structures include differing arrangements of struts, crowns, links and other structures which together form a balloon expandable stent, or stent body, and can be modified according to the methods described herein. The scaffold can also be self-expandable, or self-expandable prior to balloon expansion, or can self-expand to a second larger diameter than a first deployed diameter after recoil from said first deployed diameter. The scaffold structures (e.g. struts) have luminal and abluminal surface regions and two side surface regions extending between the luminal and abluminal surface regions as can be seen in the cross sectional views of FIGS. 2-9. Stent structural elements, may have a thickness of 100 micrometer, but the thickness can range from 25 micrometer to 500 micrometer, or from 75 micrometer to 300 micrometer, or preferably from 100-200 micrometers. The strut length (the longest dimension) may be 0.75 mm, but strut length can range from 0.35 mm to 3 mm, preferably from 0.5 mm to 1.5 mm, or other. The width of stent structural elements may be 150 micrometer, but can range from 50 to 500 micrometer, from 100 to 300 micrometers or from 150 to 250 micrometers.

Other embodiments of scaffolds and materials and treatments therefore are described in further detail in U.S. Pat. Nos. 8,182,890; 8,323,760; 8,636,792; 8,814,930; and U.S. Patent Publication Nos. 2008/0177373 and 2006/0029711 which have been previously incorporated by reference herein.

Figure 17:
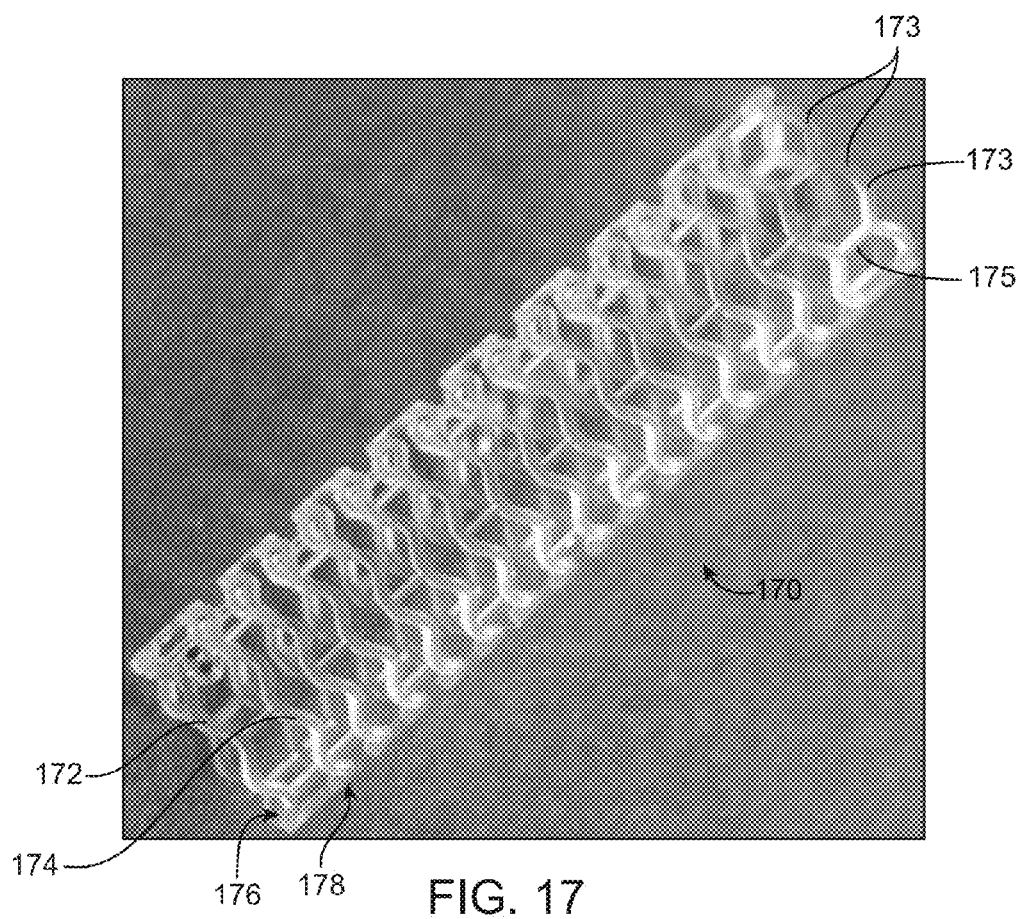
FIG. 17 is a perspective view showing an example of a stent prosthesis showing the stent pattern.

An exemplary patterned stent 170 is shown in FIG. 17. The patterned stent, stent or stent body 170 has struts 174 joined by crowns 172. The patterned stent has luminal surface regions 176 facing the lumen of the blood vessel, and abluminal surface regions 178 which face the blood vessel wall or faces the lumen wall. Each of the scaffold structures such as struts, crowns, and links, has two side surface regions extending between the luminal and abluminal surface regions. The rings 173 each comprise struts 174 joined by crowns 172. The rings 173 can be in-phase or out-of-phase or a combination thereof and are interconnected by links 175. A ring 173 is connected to an adjacent ring by links 175, or also some adjacent crowns are connected by links 175. Some of the links 175 may be attached to or replaced by one or more loops each containing one, two or more axially or radially displaced radiopaque markers, or radiopaque markers may be placed in the end rings of the patterned stent. The patterned stent 170 is balloon expandable and has low recoil, sufficient radial strength to support a body lumen or blood vessel, conformability to the body lumen or blood vessel, and low percent shortening upon expansion of less than 15%.

Many other stent patterns including differing arrangements of struts, crowns, links and other structures which together form a balloon expandable structure are possible. Two such examples are shown in FIGS. 18 and 19.

Figure 18:
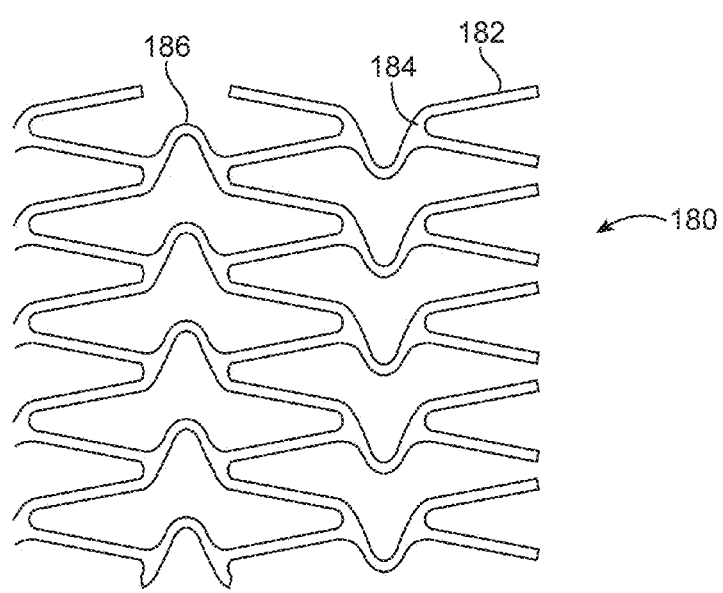
FIG. 18 is a two dimensional top view showing an example of a part of a stent prosthesis, showing the stent pattern.

FIG. 18 depicts a two dimensional view of a part/portion of a patterned stent 180 having a plurality of struts 182 joined by crowns 184. As shown in FIG. 18, the crowns 184 are connected by U-shaped links 186 which alternate in directions (upward and downward directed) depending on axial location along the length of the stent. The U-shaped links 186 may be replaced with straight, S-shaped, W-shaped or other shaped links and may be positioned at every crown or at some crowns, every other crown, or other numbers of crowns. In addition to links connecting adjacent rings, typically connecting adjacent crowns of adjacent rings, links can also connect/interconnect struts to other struts or crowns of adjacent rings. In addition to or as an alternative to rings, or serpentine ring patterns, helically wound rings, or helically wound serpentine patterns can also be used.

Figure 19:
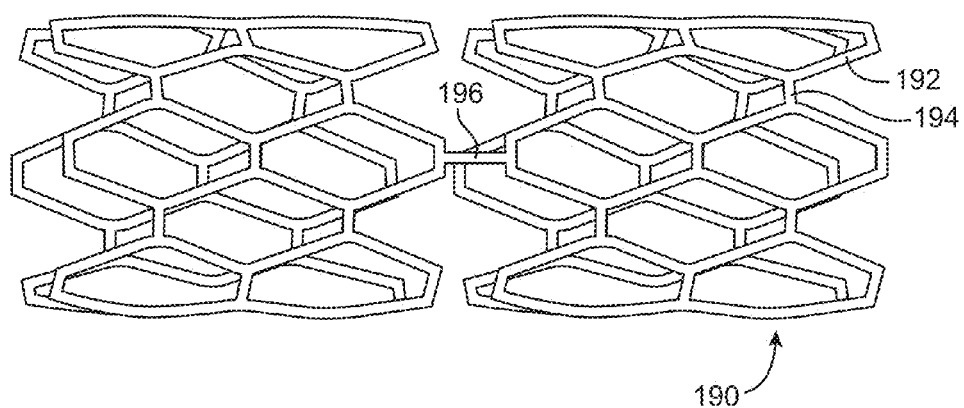
FIG. 19 is a side perspective view showing another example of a stent prosthesis showing the stent pattern.

FIG. 19 depicts another example of a patterned stent 190 having struts 192 and crowns 194 joining struts. Optionally as seen in the patterned stent of FIG. 19, link 196 connects two adjacent crowns. The links 196 may be straight, sinusoidal, or other shaped. One, two or more links 196 can connect the stent rings. The struts shown in the stent examples of FIGS. 1 and 17-19 are straight; however some or all of these straight struts can be replaced by curved or other shaped struts. Struts can be axially aligned in a crimped configuration or can be at an angle to the longitudinal axis. Upon expansion of the stent, generally the angle between the struts and the longitudinal axis of the stent increases.

In a stent pattern, generally crowns join struts, for example crowns may join two struts or three or four struts, or other. Crowns can be straight, arc, semi-circular, or key hole shaped, or other crown shapes that connect struts. Struts can be straight, wavy, or other strut shapes. Struts may extend axially, in a helical direction, or other direction such as between an axial direction and a radial direction. Crowns can be connected to adjacent crowns. Crowns may be connected to adjacent crowns by a link, such link can be straight links, or have other shapes such as U, V, W, S, or other shapes or geometries. Crowns connected to adjacent crowns by links typically connected on any points or areas along the length of the crown may be connected to adjacent crowns without a link, at the point of intersection of the adjacent crowns or at any other point along the length of the adjacent crowns where they meet. Crowns may be connected to adjacent crowns by fusing the two crowns into one, such as in the embodiment of FIG. 19.

The terms "scaffold structures", and "stent elements" as used herein comprise stent structural elements such as struts, links, crowns, elements or other structural components of the stent prosthesis. Together these stent structural elements form a stent, scaffold, stent body or prosthesis body.

The term "bulbous" or as used herein means resembling a bulb in shape, curving outwardly in a convex shape, protruding, protruding outwardly, extending, extending outwardly, bulging, bulb like, bulb shape, swelling, outwardly protruding or extending in a convex shape. A "dogbone" shape has opposed bulbous ends which need not necessarily be of the same size, shape or be uniform or symmetrical.

The term "concave" as used herein means hollowed or rounded inward like the inside of a bowl, sphere, circle, or other geometric shape such as an ellipse or parabola, arched in or curving in, and also may include a stepped series of surface regions which together form a concave shape.

The term "convex" as used herein means curved outward the exterior of a bowl sphere, circle or other geometric shape such as an ellipse or parabola, arched out or curving out, and also may include a stepped series of surface regions which together form a convex shape.

The surface region that has a concave or convex shape may be a smoothly continuous surface region, a surface region that has a concave or convex shape may have one or more discontinuities, depressions, protrusions or other perturbations, provided that the overall shape or form of the surface region is concave or convex shape. The bulbous surface regions may in some instances have one or more discontinuities, depressions, protrusions or other perturbations, provided that the overall shape or form is bulbous.

In disclosed embodiments, surface regions of a stent structural elements created during laser cutting are modified to provide a shape which improves mechanical performance of the scaffold and/or provides improved drug delivery from the scaffold or from a coating on the shaped scaffold. The modified surface regions formed by the methods described herein may occur on some or substantially all stent structural elements.

The flat side surface regions extending between the luminal and abluminal surface regions of the stent structural elements (e.g. struts, crowns, links and/or other structures) of the scaffold created by a fabrication process such as laser cutting can be modified to form convex side surface regions, preferably convex side surface regions substantially along the thickness of the stent structural element. The convex side surface regions in either the convex or bulbous shape function to more widely distribute tensile stresses and compressive stresses along the scaffold and can increase radial strength of the scaffold. The dimension of a stent structural element between the luminal and abluminal surface regions is the thickness of the stent structural element. In some instances, the convex or bulbous shape of the side surface regions joining the abluminal and luminal surface regions may have a flat portion in about the middle of the side surface between the abluminal and luminal surface regions.

The flat or slightly convex abluminal surface regions of the stent structural elements can be modified by the processes/treatment described herein to form concave or flat abluminal surface regions. The flat or slightly concave luminal surface regions of the stent structural elements can be modified by the processes/treatment described herein to form concave luminal surface regions. In some instances, the concave shape of the abluminal surface region may have a flat portion at about the middle of the abluminal surface region or at about the middle of the width between the two side surface regions. Concave abluminal surface regions can provide benefits in drug coating and in drug delivery and benefits of embedding the scaffold into the vessel wall and convex side surface regions can provide benefits in retaining the scaffold on a balloon catheter, and also improved trackability in tortuous anatomy. Convex side surface regions make it easier to insert the stent on the catheter into and through the blood vessel to the desired location. The dimension of a stent structural element between its side surface regions is the width of the scaffold structure. The concave curvature of the abluminal and/or luminal surface regions extends substantially across the width of these surface regions.

The stent prosthesis may be further coated with a coating comprising at least one drug and at least one polymer, wherein the coating follows the contour of the underlying surface region, in a preferred embodiment, without substantially changing the luminal, abluminal or side surface region shapes.

The substantially flat luminal and abluminal surface regions of the stent structural elements can be modified by the processes described herein to form substantially dumbbell, barbell, bow tie, or dogbone shaped stent structural elements or cross section stent structural elements.

Figure 2:
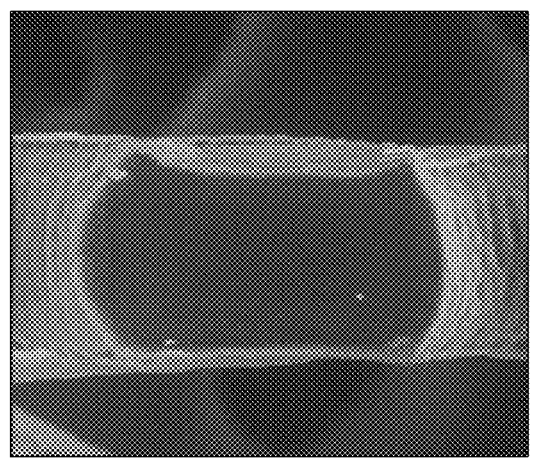
FIG. 2 is an SEM image showing a cross section of a stent structural element in this image, showing a bulbous region extending between the abluminal surface region and the luminal surface region.

FIG. 2 is an SEM image showing a cross section of a stent structural element which has been modified to have a shape designed for improved scaffold performance. The stent structural element of FIG. 2 has a luminal surface region (bottom), an abluminal surface region (top), and two side surface regions. As shown in FIG. 2, the abluminal surface region is substantially concave across the width of the abluminal surface region while the two side surface regions are substantially convex across the thickness of the side surface regions of the strut. This fabricated shape or modified/treated shape can distribute tensile stresses and compressive stresses along of the scaffold and can provide improved radial strength of the scaffold. The SEM image of FIG. 2 is taken at a magnification of 1200× to show the stent structural element features at the micrometer level.

Figure 20:
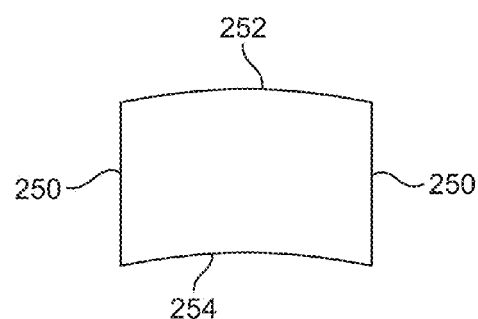
FIG. 20 is an example of a stent structural element, for example a strut, cross section before treatment.

FIG. 20 shows an example of a cross section of a stent structural element before modification or treatment when the strut is a part of a stent formed from a tube. The abluminal surface region 252 of the untreated stent structural element is slightly convex due to the overall curvature of the tube. Similarly, the luminal surface region 254 is slightly concave due to the curvature of the tube. The side surface regions 250 extend from the abluminal to the luminal surface regions and may be parallel or non-parallel depending on the process used to form the tubular stent but are generally flat/straight.

In embodiments, the modification of the scaffold surface region shapes improves tracking (maneuverability) and/or push by reducing the force required to track or push the scaffold mounted on a catheter through a cylindrical body, such as a blood vessel. The reduction of track or push force is achieved because of the changing of the area of surface region contact between the modified scaffold shape and the vessel. On the abluminal side, the unmodified surface regions on the scaffold structure can act like ratchet elements as the scaffold is pushed through a blood vessel, especially one with calcified lesions. This may hinder tracking or movement through the vessel because the unmodified side regions can get caught on the walls of the vessel. On the luminal side, the unmodified side regions of the scaffold can inhibit a guidewire or catheter from going through one of the spaces between scaffold structures, such as for treatment of a bifurcation. In order to improve tracking or passage of guidewire and catheter, it is beneficial to modify the shapes of the surface regions on the scaffold structure. The modification of the shape of the surface regions to provide convex surface regions, concave surface regions or a combination thereof improves performance of the scaffold.

Examples of processes which can be used to shape the surface regions of the scaffold structures include solvent treatment, media blasting, abrasive tumbling, mechanical shaping, laser shaping, heat treatment or other shaping processes. The processes of shaping the surface regions of the scaffold create substantially convex side surface regions extending from the luminal to the abluminal edge. The convex side surface regions can have radii of curvatures of about 0.020 to about 0.375 mm, about 0.030 to about 0.200 mm, or about 0.050 to about 0.175 mm. The processes of shaping the surface regions of the scaffold can also create substantially concave abluminal surface regions extending between the side surface regions. The concave luminal and/or abluminal surface regions can have radii of curvatures of about 0.020 to about 0.500 mm, about 0.030 to about 0.200 mm, or about 0.050 to about 0.175 mm. The concavity of the abluminal surface regions may extend substantially across the width from one side surface region of the scaffold structure to the other side surface region of the same structure, with a single concave depression, or a concave shape. Similarly, the convexity of side surface regions of the scaffold structures may extend across the thickness substantially from the luminal to the abluminal surface region of the same structure as one convex surface region, or as a convex shape.

The scaffold structures can be shaped before and/or after the application of a polymer/drug coating layer to the exterior of the scaffolding. The shape treatment may be performed on the scaffold structure followed by coating with drug matrix coating wherein the coating process does not substantially change the shape of the surface regions but conforms to the concave and convex shapes of the treated surface regions.

The concave luminal surface regions after the treatment process may have a concave shape with a radius of curvature different than the radius of curvature of the inner diameter of the tube from which the scaffold is formed.

The ratio of radius of curvature of at least a portion of the luminal or abluminal surface region of the scaffold structure to the radius of curvature of the side of the scaffold structure may be less than one.

The ratio of radius of curvature of at least a portion of the luminal or abluminal surface region of the scaffold structure to the radius of curvature of the side of the scaffold structure may as another possibility be greater than one.

As another possibility, the radius of curvature of at least a portion of the luminal or abluminal surface region of the scaffold structure may be substantially equal to the radius of curvature of the side of the scaffold structure.

The radius of curvature of at least a portion of the concave luminal or abluminal surface regions may be greater than the radius of curvature of at least a portion of the convex side surface regions.

The cross section of a scaffold structure (stent structural element), may form a substantially dumbbell, barbell, bow tie, scalloped or dogbone shaped cross section structure.

Examples of shaped cross sections of scaffold structures are shown in FIGS. 3-9 each having a surface with a luminal surface region, an abluminal surface region, coupling portions coupling the abluminal and luminal surface regions, and a thickness between said luminal and abluminal surface regions; wherein at least a part of at least some of the coupling portions is bulbous. These scaffold structures can represent any scaffold structure including struts, crowns or/and links. The scaffold structure cross section shown in FIG. 3 includes a concave abluminal surface region 32 and a concave luminal surface region 34 and two convex side surface regions 30 extending between the luminal and abluminal surface regions of the scaffold structure. The convex shape of the side surface regions 30 extends substantially across the thickness of the scaffold structure to provide two bulbous regions. The concave shape of the abluminal and luminal surface regions 34, 32 extends substantially across the width of the scaffold structure.

The scaffold structure cross section shown in FIG. 4 includes two convex side surface regions 40, as well as a concave abluminal surface region 42 and a substantially flat luminal surface region 44 so that bulbous coupling portions are provided by the abluminal surface region 42 and the side surface regions 40. The scaffold structure cross section of FIG. 5 includes two convex side surface regions 50, as well as a substantially flat abluminal surface region 52 and a concave luminal surface region 54 so that bulbous coupling portions are provided by the luminal surface region 54 and the side surface regions 50. The scaffold structure cross section of FIG. 6 includes substantially flat side surface regions 60, as well as a concave abluminal surface region 62 and a concave luminal surface region 64 so that bulbous coupling portions are provided by the abluminal surface region 62 and the side surface regions 60 and by the luminal surface region 64 and the side surface regions 60. The scaffold structure cross section of FIG. 7 includes convex side surface regions 70, as well as a concave abluminal surface region 72 and a concave luminal surface region 74 so that bulbous coupling portions are provided by the abluminal surface region 76 and the side surface regions 70 and by the luminal surface region 74 and the side surface regions 70. The concave abluminal and luminal surface regions 72, 74 may include a substantially flat center portion 76 which forms a bottom part of the concave surface region. Similarly, the convex side surface regions 70 can include flat portions. The scaffold structure cross section of FIG. 8 includes two concave side surface regions 80, as well as a concave abluminal surface region 82 and a concave luminal surface region 84 so that bulbous coupling portions are provided by the abluminal surface region 82 and the side surface regions 80 and by the luminal surface region 84 and the side surface regions 80.

The scaffold structure cross section of FIG. 9 includes substantially convex side surface regions 90, as well as a concave abluminal surface region 92 and a concave luminal surface region 94 and rounded intersection of the concave and convex surface regions, which together form a dogbone shaped cross section so that bulbous coupling portions are provided by the side surface regions 90. In the example of FIG. 9, the shape of the scaffold structure is such that it can embed or nest the scaffold into the vessel wall upon expansion providing better scaffold apposition to the surrounding tissue. In contrast, square or rectangular flat cross section abluminal scaffold structure surface regions may inhibit embedding because the substantially flat surface regions push on the uneven plaque covered vessel wall during expansion.

The convex and/or bulbous surface regions of the cross sections depicted in FIGS. 3-9 can distribute tensile stresses and compressive stresses along of the scaffold and can provide improved radial strength of the scaffold. Although the cross sections of FIGS. 3-9 have been shown as symmetrically shaped about a midline of the scaffold structure, the cross sections can also be asymmetrically shaped. At least a portion of the scaffold structure with a concave abluminal surface region may have a minimum cross sectional thickness of between 50 to 300 micrometers, preferably between 75 to 200 micrometers, more preferably from 100 to 150 micrometers.

At least a portion of the scaffold structure with a concave abluminal surface region may have a maximum cross sectional thickness of between 50 to 500 micrometers, preferably between 75 to 300 micrometers, more preferably from 100 to 200 micrometers.

At least a portion of the scaffold structure with a convex side surface region may have a minimum cross sectional width of between 50 to 300 micrometers, preferably between 75 to 300 micrometers, more preferably from 100 to 150 micrometers.

At least a portion of the scaffold structure with a convex side surface region may have a maximum cross sectional width of between 50 to 500 micrometers, preferably between 75 to 300 micrometers, more preferably from 100 to 200 micrometers.

Measurements described herein of the dimensions including widths, thicknesses, radii of curvature and the like may be made on the actual prosthesis or on enlarged views of the prosthesis by SEM or microscope, such as the SEM 1200× image in FIG. 2. Other means of viewing the bulbous region, convex side surface region, or concave abluminal surface region can also be accomplished using microscope or micro view at magnifications ranging from 10×-1500×.

After the shaping process treatment, the variance in scaffold structure dimensions along the length of the scaffold may be less than 40%, preferably less than 25%, more preferably less than 10%.

In some embodiments, the tubular body, stent or scaffold may be formed from at least one biodegradable polymer or other biodegradable material having desired degradation characteristics where the polymer may be modified to have the desired crystallinity, Tg, recoil, strength, shortening, expansion characteristics, crimping characteristics, molecular weight, and/or other characteristics. Biodegradable polymers include one or more polymers, copolymers, blends, and combination thereof of: lactides, caprolactones, and glycolides. Some examples include poly-DL-Lactide, polylactide-co-glycolactide; polylactide-co-polycaprolactone, poly (L-lactide-co-trimethylene carbonate), polylactide-co-caprolactone, polytrimethylene carbonate, elastin, fibrin, collagen and copolymers; polyhydroxybutyrate; polyhydroxyvalerate, poly orthoesters, poly anhydrides, polyiminocarbonates and the like. One example of a biodegradable polylactide based polymer comprises a copolymer of L-lactide and glycolide, preferably with a weight ratio of 85% L-lactide to 15% glycolide. Another example of a biodegradable polylactide based polymer comprises a copolymer of L-lactide and caprolactone, preferably with a weight ratio of 90% L-lactide to 10% caprolactone.

In one example, the tubular body, stent or scaffold comprises a degradable polymeric material wherein the polymeric material comprises one or more polymers; or one or more copolymers; or one or more blends of monomers, polymers or copolymers; and combinations thereof. The polymeric material may comprise one or more polymer or one or more co-polymer. Additionally, at least one monomer, polymer, or co-polymer of similar material (to the one or more polymer or the one or more co-polymer) is blended with the polymeric material.

In another example, a biodegradable stent comprising a polymeric material comprises a copolymer of lactide and caprolactone in the ratio by weight ranging from 80-99% lactide to 1-20% caprolactone; wherein the polymeric material further comprises a monomer or polymer including a copolymer of one or more of the following: lactide, glycolide, lactide glycolide, caprolactone, and lactide caprolactone; wherein the one or more monomer or polymer total amount is 1 to 100 micrograms per milligram of polymeric material, preferably 5 to 75 micrograms per milligram of polymeric material, more preferably 10 to 50 micrograms per milligrams of polymeric material; wherein the scaffold with the modified structure cross section is capable of being crimped from an expanded configuration to a smaller crimped configuration, and at body temperature capable of being expanded to a deployed configuration, and having sufficient strength when expanded to support a body lumen, without fracture of the stent.

The one or more monomer and/or polymer may change (increase or decrease) the crystallinity of the polymeric material by 5% to 150%, preferably by 10% to 75%, more preferably by 10% to 50%. In another example, the one or more monomer and/or polymer controls the crystallinity of the polymeric material to between 1% and 55%, preferably between 1% and 35%. In a further example, the one or more monomer and/or polymer does not change the crystallinity of the polymeric material from being between 1% and 55%. The one or more monomer and/or polymer may not substantially change the Tg of the polymeric material. Alternatively, the one or more monomer and/or polymer changes (increases or decreases) the Tg temperature of the polymeric material by 1° C. to 15° C., preferably 1° C. to 10° C., more preferably by 1° C. to 5° C. In an example, the one or more monomer and/or polymer controls the Tg temperature of the polymeric material to between 20° C. and 55° C., preferably to between 35° C. and 50° C., more preferably to between 37° C. and 50° C., most preferably between 37° C. and 45° C.

In other examples, the tubular body, degradable stent or scaffold may comprise at least one non-degradable polymer where the polymer may be modified to have the desired crystallinity, Tg, recoil, strength, shortening, expansion characteristics, crimping characteristics, molecular weight, and/or other characteristics. Non-degradable polymers include for example, a silicone-urethane copolymer, a polyurethane, poly(ethylene), phenoxy, ethylene vinyl acetate, chondroitin sulfatepoly(vinylidene fluoride), poly(vinylidene fluoride-co-hexafluoro propene), poly(tetrafluoroethylene), expanded poly(tetrafluoroethylene), poly(sulfone), polymethylmethacrylate, poly(n-butyl methacrylate), poly(N-vinyl pyrrolidone), copolymers of vinyl monomers and olefins such as poly(ethylene-co-vinyl alcohol) (EVAL), copolymers of acrylonitrile-styrene, ABS resins, and copolymers of ethylene-vinyl acetate, poly(amides) such as Nylon 66 and poly(caprolactam), alkyd resins, poly(oxymethylenes), poly(imides), poly(ester amides), epoxy resins, polyurethanes, rayon, and rayon-triacetate.

In other examples, the tubular body, biodegradable stent or scaffold may comprise at least one degradable or non-degradable biological molecule where the material may be modified to have the desired recoil, strength, shortening, expansion characteristics, crimping characteristics, molecular weight, and/or other characteristics. Biological materials include, for example, albumin, fibrin, fibrinogen, starch, poly(amino acids), peptides, proteins, gelatin, elastin, chondroitin sulfate, dermatan sulfate (a copolymer of D-glucuronic acid or L-iduronic acid and N-acetyl-D-galactosamine), collagen, hyaluronic acid, glycosaminoglycans, polysaccharides, chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

In other examples, the tubular body, biodegradable stent or scaffold may comprise at least one degradable metal where the degradable metal has a desired recoil, strength, shortening, expansion characteristics, crimping characteristics, molecular weight, and/or other characteristics. Degradable materials for the metal stent include can be a suitable metal such as magnesium, zinc, iron, and alloys or combinations thereof. The metal can be modified to exhibit different hardnesses, and thus varying stiffnesses, by well-known annealing and manufacturing processes. The tubular body may also comprise combinations of biodegradable polymeric materials and degradable metals.

The degradable stent prosthesis may comprise a metal or metal alloy, optionally formed from a tubular body, wherein the metal or metal alloy comprises zinc, magnesium, and/or iron, or alloys, wherein the stent is treated to modify at least some abluminal surface regions making them concave substantially across the width of said abluminal surface regions, and/or modifying at least some of side surface regions making them substantially convex across the thickness of said side surface regions.

The above surface region modification may be performed without substantially changing weight or mass of the prosthesis compared to the weight or mass of the prosthesis before treatment, or without losing more than 15% in weight or mass after treatment, or without substantially losing more than 25% in weight or mass after treatment.

Degradable metal and metal alloys can be treated using the methods described in this application. In addition, treatments using acid such as nitric acid, hydrochloric acid, phosphoric acid and/or sulfuric acid can be used to modify the abluminal surface regions to concave, and side surface regions to convex.

1. Structure Shaping by Solvent Treatment

The scaffold structures may be shaped by exposure to at least one solvent. The exposure to the solvent can be accomplished in a variety of ways such as by dipping, spraying, exposure to solvent vapor or other solvent application processes.

a. Structure Shaping by Solvent Dipping

The scaffold supported lightly on a mandrel is dipped into a first solvent for about 1 second to one minute, 1 second to 30 seconds, or 2 seconds to 10 seconds and is quickly removed. The scaffold can be rinsed in a second solvent to remove materials that are adhering to the scaffold. The solvent, solvent concentration, and time of exposure may be selected based on its ability to move the scaffold material at the side surface regions of the scaffold to the luminal and abluminal surface regions and change the shapes of these surface regions without substantially dissolving the scaffold, that is without the polymeric material dissolving (or otherwise dispersing) in the solvent and without forming a solution of polymeric material in the treatment solvent. Also the solvents, concentrations and/or combinations of solvents and time of exposure may be selected based on the particular polymeric materials utilized to achieve the desired shaping of the stent structural elements. At least a portion of the surface regions on the side, abluminal and luminal surface regions of the struts and other structures can be shaped by inserting a loose mandrel such as a Teflon rod or tube inside the scaffold to support the scaffold during the selected treatment process. Preferably, the outer diameter of the loose mandrel is 0.001" to 0.100" smaller, more preferably 0.005" to 0.015" smaller than the inner diameter of the scaffold for a 2.5 to 4.0 mm scaffold.

At least some parts of the scaffold structure width may change by up to 25%, preferably change by up to 15%, more preferably change by up to 10%. In another example, at least some parts of the scaffold structure thickness change by up to 25%, preferably change by up to 15%, more preferably change by up to 10% as a result of the treatment.

The scaffold cross section may be reduced in width and increased in thickness due to the transfer, flow, or movement of scaffold polymeric material during the solvent shaping process. In one example, the processes of shaping the surface regions of the scaffold can increase the maximum thickness of the scaffold by at least 10%, at least 20%, or at least 30%, when taken in cross section. The maximum width of the struts and other structures can remain the same while the thickness changes as described above or can decrease by at least 10%, at least 20%, or at least 30%, when taken in cross section. The treatment may cause the flow of polymeric material from one side surface region to an immediately adjacent surface region, which may be on the same strut, crown or link.

In some embodiments, the shaping process can also be due to redistribution of the scaffold material from some surface regions of the scaffold to other surface regions to create the shaped struts with convex side surface regions and concave abluminal surface regions. The solvent is selected and applied for periods of time to soften the polymeric material without dissolving it so that it flows from one surface region to another portion of the surface region or an adjacent surface region.

In some embodiments, the scaffold mass after shaping process is substantially unchanged from before the treatment process.

In other embodiments, the scaffold mass after the shaping process is decreased by no more than 25%, preferable no more than 10%, more preferably no more than 5%.

The first and second solvent can be a single solvent or a mixture of different solvents. Examples of the first solvent include methylene chloride (DCM), chloroform, tetrahydrofuran, dimethyl-sulfoxide (DMSO), acetone, toluene, xylene, DMF, or the like, or a combination thereof. The first solvent may be any solvent which can dissolve the scaffold if exposed to this solvent for more than 1 minute at room temperature. The second solvent can be any solvent or other fluid which does not measurably dissolve the scaffold if the scaffold is exposed to the second solvent for more than 1 minute at room temperature. In order to provide the shaping without dissolving the polymeric material or losing any significant amount of the polymeric material, the treatment times are about 1 second to one minute, 1 second to 30 seconds, or 2 seconds to 10 seconds followed by quick removal from the solvent.

In a preferred embodiment, the stent material is not dissolved (i.e. not permanently removed from the stent prosthesis) wherein the polymeric material flows from one surface region on a stent structural element to an adjacent surface region on the same stent structural element, or one surface region on a stent structural element to the same surface region on the same stent structural element.

The first solvent can also be a combination of a solvent that is capable of dissolving the scaffold and a solvent that does not dissolve the scaffold. For example, the first solvent can include a solvent capable of dissolving the scaffold after 1 minute or longer of exposure to the solvent at room temperature and a solvent which does not dissolve the scaffold after 1 minute of exposure at room temperature. One example of such a first solvent combination is 4 parts DCM and 6 parts Ethanol. In one example, the first solvent includes from 0.1 to 10 parts of solvent capable of dissolving the scaffold (such as DCM) and 9.9 parts to 0.1 parts of solvent not capable of dissolving the scaffold (such as Ethanol). The second solvent can be ethanol, methanol, isopropanol, water, aqueous solution, or the like, or combinations therefore.

The scaffold shaping process may utilize a mixture of solvents to modify the scaffold structure cross section due to the transfer of scaffold material from its width to its thickness.

The scaffold shaping process may utilize at least one solvent to initiate the modification of the scaffold structure cross section due to the transfer of scaffold material from its width to the thickness and at least another solvent to terminate the process.

Instead of using a second solvent, the scaffold on a mandrel can be shaken or blown with gas to remove excess solvent and/or dried in vacuum, oven, and or pressurized $CO_2$. Instead of a second solvent, the scaffold can be quickly placed in an oven, vacuum oven, freeze dried or exposed to another known process to remove the first solvent.

Not all of the first or second solvent needs to be removed after the dipping treatment is complete. Additional processes which can be used to remove solvent include heat treatment, exposure to carbon dioxide, freeze drying or vacuum. The scaffold can be transferred to a bigger, tighter mandrel to maintain the dimensions of the scaffold for additional drying such as drying at ambient temperature, elevated temperature, such as below the glass transition temperature of the polymer in an oven, vacuum oven, freeze drying or the like, in a vacuum, or other means.

The scaffold can also be further treated by placing on a tight mandrel and dipping to further shape the abluminal and side surface regions as will be described further below. Additional shaping of the side, abluminal and luminal surface regions of the crowns and axial struts can be achieved by repeating a dipping treatment more than once or by dipping for longer periods of time. Agitating during the dipping treatment can increase the rate of shaping. Spinning or rotating of the scaffold in the solvent can help achieve a more consistent application of the solvent along the length of the scaffold and particularly in tight spaces of the scaffold. Spinning can also change the distribution of the material during shaping, for example to provide a strut shape with a wider abluminal side due to forces on the outer material of the scaffold during spinning. The scaffold can be treated while oriented in the solvent horizontally, vertically, at an angle or in a combination of orientations to achieve a desired shaping.

The scaffold may be rotated around its own axis and/or revolved around in a chamber with solvent to control the shaping of the scaffold structure cross section.

As an alternative or additionally to spinning or rotating the scaffold, the solvent media can flow relative to the scaffold, or a combination of rotating the scaffold and causing solvent to flow can be used to achieve the desired effect. The scaffold and the solvent can both move relative to each other. Examples of this would be a revolving scaffold on a rotating mandrel in a solvent bath which is being stirred with a stir bar.

Figure 10:
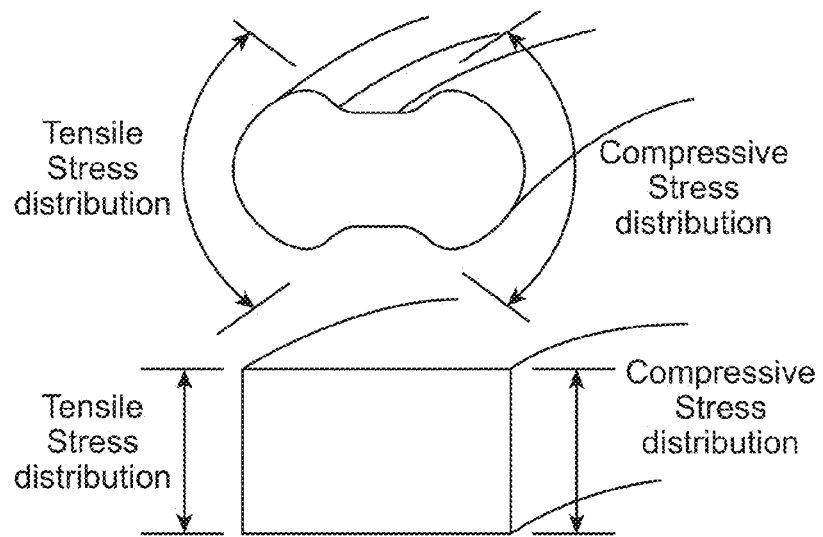
FIG. 10 is a schematic illustration of the difference in tensile and compressive stress distribution between a treated and untreated stents.

FIG. 2 illustrates a cross section of a stent structural element after treatment according to one example. In this figure, the treatment provides a concave abluminal surface region across substantially the width of the abluminal surface region; it also provides convex side surface regions across the thickness of the side surface regions. These shapes allow the distribution of tensile and compressive stresses over a greater area as shown in FIG. 10. As shown in FIG. 10, the surface region area over which the tensile and compressive stresses are distributed during bending of the stent structural element is increased due to the convex side surface regions and this leads to increased radial strength of the scaffold. In an example, a scaffold with modified cross section has increased radial strength by at least 5%, at least 10% or at least 20% over scaffolds without modified cross section. The treatments described herein can increase the radial strength of the scaffold by at least 5%, at least 10% or at least 20%.

The first and second solvents and the processes for dipping and removing solvent can vary depending on the desired scaffold cross sectional shape.

One advantage of the abluminal shaping is the increased drug delivery to the walls of the lumen which can be achieved with a concave abluminal surface region. The abluminal concave surface region can help direct drug delivery to the lumen wall. The edges of the concave abluminal surface regions such as those shown in FIG. 2 can have a ledge which further helps to direct drug delivery to the lumen wall. This focuses drug delivery using concave abluminal surface regions.

b. Luminal and Side Shaping by Solvent Dipping

Shaping of or enhancing the luminal shape and/or shaping the side surface regions of the scaffold struts, crowns and other structures without abluminal shaping can be achieved by placing a tube such as Teflon tube over the scaffold (or otherwise masking the surface areas not to be treated). The outer tube should be tight fitting so that no significant amount of fluid can pass between the outer surface regions of the scaffold and the inner surface region of the tube. Optionally, a looser mandrel such as a Teflon rod or tube can be inserted inside the scaffold as a support for handling purposes. Preferably, the outer diameter of this looser inner mandrel is 0.001" to 0.100" smaller, more preferably 0.005" to 0.015" smaller than the inner diameter of the scaffold. The scaffold sheathed with the outer tube and supported lightly on the inner mandrel is then dipped into a first solvent for about 1 sec and quickly removed and preferably rinsed in a second solvent to remove materials that are adhering to the scaffold according to any of the methods and with any of the solvents described above with respect to the previous processes.

Figure 11:
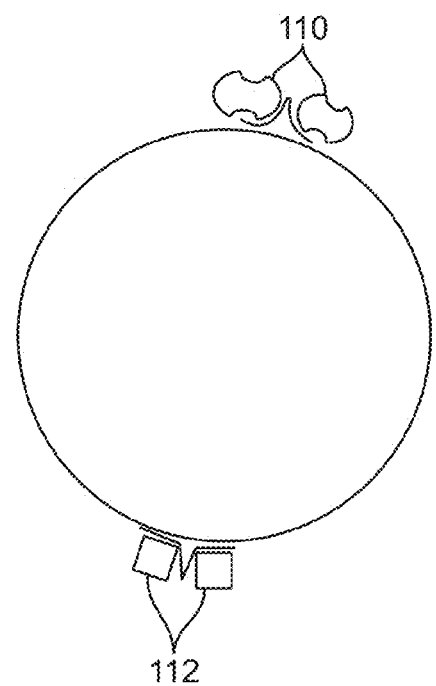
FIG. 11 is a schematic cross section of a balloon showing a pair of struts having modified/treated surface regions and a pair of struts having unmodified surface regions.

Shaped luminal surface regions and shaped side surface regions can provide an improved surface region for contact with a delivery system, such as a balloon catheter. The convex side surface regions provide greater contact than square or rectangular flat surface regions between balloon material of the delivery system and the scaffold. FIG. 11 illustrates a balloon with a pair of stent structural elements 110 having modified luminal surface regions and convex sides and a pair of stent structural elements 112 having flat surface regions. In the process of crimping the scaffold onto the balloon a portion or flap of balloon material extends between the stent structural elements. As can be seen in FIG. 11, there is increased surface region area of contact between the modified stent structural elements 110 with convex sides and the balloon flap than with the flat surface regions of the stent structural elements 112. This provides improved scaffold retention on a balloon catheter in a crimped configuration by using a shaping processing step.

Additionally, the concave luminal surface regions of the scaffold structures can also improve stent retention on a balloon or other delivery system by providing a form of suction or vacuum surface region which adhere the modified scaffold better to the balloon.

c. Solvent Vapor Shaping

The scaffold can be exposed to vapors of a solvent for an amount of time sufficient to provide a desired shaping of the scaffold structures. In the solvent vapor shaping method, the scaffold is placed adjacent to a bath of liquid solvent in a solvent chamber. The solvent is selected to be a solvent which can dissolve the scaffold at least in part if the scaffold is placed in the solvent for one minute. However, in this method, it is the vapors from the solvent which come in contact with the crowns, axial struts and other portions of the scaffold and redistribute the material of the scaffold to provide convex side surface regions, concave luminal and/or abluminal surface regions. The solvent or the entire vapor chamber can be heated to accelerate vaporization of the liquid solvent in the liquid bath. Alternatively, the solvent vapor can be provided into the chamber in a gaseous form alone or with other gases. The time of exposure of the scaffold to solvent vapor can be greater than 10 mins, greater than 30 mins, greater than 1 hour, greater than 24 hours, or greater than 48 hours.

As an example, the scaffold may be rotated around its own axis and revolved around in a chamber with solvent vapor to control the shaping of the scaffold structure cross section.

After the solvent vapor shaping process is complete, excess solvent can be removed by a second solvent, heating, drying or any of the methods discussed herein. In one example, the solvent chamber can be pressurized to increase the amount of solvent vapor in contact with the scaffold.

The exposure of only a portion of the scaffold to the solvent vapor, such as by inserting a tight tube inside the scaffold or inserting the scaffold inside a tight tube (or any other suitable form of masking) can preferentially shape the surface regions on the luminal or abluminal sides of the scaffold. Other masking methods can also be used.

The solvents employed in the solvent vapor smoothing process can include any of the solvents described above. Particularly useful solvents are those that can be provided in a gaseous form at a temperature of less than the Tg of the scaffold material.

d. Solvent Spraying

The scaffold can be exposed to solvent by spraying with the solvent to shape the surface regions of the stent structural elements and redistribute the scaffold material. Spraying of solvent can be performed with any spray apparatuses, such as those that are known for application of drug/polymer coatings to stents. The sprayed solvent may be any of the solvents described herein which are capable of dissolving a portion of the scaffold structure.

Solvent spraying from an exterior of the scaffold can result in preferential shaping with the abluminal surface regions experiencing greater concave shaping than the luminal surface regions. In one example, abluminal surface regions have a concave radius of curvature greater than luminal surface regions. Solvent spraying can also be from an interior of the scaffold by passing a spray nozzle into the interior of the scaffold and moving it along the length of the scaffold interior. Masking of portions of the scaffold may also be used to get preferential shaping of some surface regions over other surface regions.

In one example, a flow rate of solvent sprayed onto the scaffold is higher than typically use for coating a stent. Flow rates of at least 20 ul/min (microliter/minute), at least 30 ul/min, or preferably at least 75 ul/min, or more preferably at least 100 ul/min can be used.

A loose mandrel can be placed inside the scaffold during spraying to maintain the shape of the scaffold as the solvent is sprayed onto the surface regions.

The scaffold can be rotated and/or moved longitudinally during spraying. In one example, the scaffold is rotated and moved in a crisscross fashion during spraying to achieve uniformity of shaping and to prevent large amounts of material from being dissolved or redistributed too quickly. Air can be blown at the scaffold to remove any excess solvent during and/or after spraying of the solvent. Removal of excess solvent can be performed by any of the processes described herein.

e. Other Solvent Application

In addition to application of solvent by dipping, spraying, or application of solvent vapor, solvent can be applied to a scaffold to provide shaped scaffold in other manners including ink jet printing, painting, gel application or the like.

Some of the solvent application methods described herein can apply solvent only to portions of the scaffold while leaving other portions of the scaffold untreated such as preferentially shaping and/or smoothing only the luminal or only the abluminal surface regions. In another example, the treatment is applied only to the crowns to further enhance the convex side surface regions of the crowns as these are the areas most likely to affect tracking of the stent through the vasculature. The treatment can also be used to preferentially treat different longitudinal sections of the scaffold to achieve a scaffold with differing performance along its length. In one example, the ends of the scaffold are treated to achieve a scaffold with greater radial strength at the scaffold ends.

2. Media Blasting

Shaping of the scaffold surface regions can also be performed by material removal or material compacting from the scaffold by various media blasting techniques. Material removal from or compacting of the scaffold crowns or axial struts of a scaffold to create convex side surface regions, and concave abluminal surface regions can be achieved using equipment such as a sandblaster, media blasting machine, or similar equipment which propels particles at the scaffold. The blasting treatment propels small, abrasive particles toward the scaffold in a particular pattern which matches the regions of the scaffold to be shaped.

Examples of particles which can be used include evaporable particles, such as dry ice, salt, sugar, sodium bicarbonate, combination thereof, or the like which will either vaporize or can dissolve in water. The use of dry ice or another evaporable particle as the media particles which will turn gaseous at ambient temperature eliminates the need for removal of the blasting particles after the surface region shaping process. In some examples, the evaporation of the evaporable particles may be assisted by application of heat, vacuum, or the like. The use of dry ice as the media particles can eliminate the need for removal after the shaping process because the dry ice will turn gaseous at ambient temperature.

Other blasting media can include polymeric particles such as polyethylene, polypropylene, polyethylene glycol, polyvinyl alcohol, polyvinylacetate, polyvinyl chloride, cellulose, copolymers of these, combination thereof, or the like which will dissolve in a solvent that does not immediately dissolve the scaffold such as ethanol, methanol, propanol, THF, acetone, or the like. Exposure to solvent after blasting with polymeric particles can remove particles that become at least partially embedded on the surface region of the scaffold. The media particles preferably can dissolve in a solvent in a period of less than 1 minute and the solvent is selected such that the scaffold does not dissolve in the solvent when the scaffold is exposed to solvent for 1 minute or longer.

A size of the blasting particles using screened mesh sizing can range from 60 to 600 mesh, from 100 to 550 mesh, or preferably from 150 to 500 mesh. The mesh sizes referenced herein are from standard mesh sizes, such as US Sieve Series and Tyler Mesh Size, used to classify particle size.

The size of the blasting particles impacting the surface region of the scaffold range from 250 micrometers to 10 micrometers, preferably from 100 micrometers to 20 micrometers, more preferably from 50 micrometers to 25 micrometers.

In one example, instead of focusing the blasting particles on the edge during sandblasting, a mask can cover the majority of the scaffold surface region but exposes only a portion of the edges of the crowns or axial strut. The mask can be applied by ink jet printing technologies. The covered scaffold is then sandblasted to remove only material on the edge. Preferably sandblasting is done at an angle. The mask can then be removed by any known means, such as by application of a solvent which dissolves the mask without dissolving the scaffold. After removal of the mask the resulting convex side surface regions and concave luminal and abluminal surface regions are exposed.

The media blasting may compact the material to provide the desired shapes without removing a substantial amount of the polymeric material from which the stent is formed.

3. Abrasive Tumbling

The scaffold surface regions can be shaped by abrasive tumbling methods. The scaffold can be placed in a tumbler, shaker, or vibrator with a lapping media, a sandblasting media, abrasives, abrasive grit, liquid lubricants, dry ice, others, or combination thereof, to form concave abluminal surface region having radii of curvatures of about 0.030 to about 0.200 mm, about 0.040 to about 0.150 mm, or about 0.040 to about 0.100 mm. Examples of abrasive media include aluminum oxide, jeweler's rouge, optician's rouge, emery, silicon carbide, diamond, glass, metal, oxides, ceramics, or the like. In the abrasive tumbling methods, one or more scaffolds are placed inside a barrel or tumbler which is placed on slowly rotating rails which rotates, shakes, or vibrates the barrel. The scaffolds within the barrel slide past each other, with the lapping media, sandblasting media, abrasives, abrasive grit, liquid lubricants, others, or combination thereof, between them. The amount and speed of the shaping depends on the coarseness of the abrasive, and the duration of the tumble, shaking, or vibrating.

The scaffolds can be cooled to make the material more brittle. The scaffold can be cooled to a temperature below 10 degrees Celsius, preferably below 0 degrees Celsius, more preferably below −50 degrees Celsius using dry ice or liquid nitrogen before and/or during tumbling.

The scaffolds can be heated to make the material softer. The scaffold can be heated to a temperature above Tg before and/or during tumbling.

In one example, a mask can be applied by ink jet printing technologies or another known process to allow selective abrasive shaping of the scaffold surface regions. The masked scaffold is then tumbled to remove only material on the selected portions. The mask can then be removed by any known means, such as by application of a solvent which dissolves the mask without dissolving the scaffold. After removal of the mask the resulting convex side surface regions and concave luminal and abluminal surface regions are exposed. As in the other shaping processed described herein, selective portions of the scaffold can be shaped without shaping other portions of the scaffold by use of mandrels, sleeves and/or masking.

4. Mechanical Shaping, Molding and Ink Jet Printing

The surface regions of crowns, axial struts, or other scaffold structures of a scaffold can be shaped or chamfered by certain mechanical tools to form shaped surface regions. The surface regions can be shaped or chamfered with a miniature tool having a sharp edge or deburring brush and small enough to fit between crowns and axial struts and scraping the tool across the surface regions. These tools can be moved robotically and controlled by a camera and an image processing system.

In another example, the tool can be a rotating miniature sanding tool which by spinning against the surface regions or edges of the crowns or axial struts creates convex side surface regions, concave luminal surface regions and/or concave abluminal surface regions.

In order to increase the hardness of polymer scaffolds or other scaffolds of soft materials for mechanical shaping according to any of the described processes, the scaffold can be held at a temperature below 10 degrees Celsius, preferably below 0 degrees Celsius, more preferably below −50 degrees Celsius using any suitable cooling method such as dry ice or liquid nitrogen.

The abluminal surface regions of the crowns of a scaffold can be shaped or chamfered by inserting a curved or flexible mandrel inside the scaffold. The scaffold in the curved position on the mandrel is then dragged over an abrasive material such as sandpaper wrapped around a cylinder, round file, deburring brush, sanding stone, or the like. As the scaffold in a curved position is abraded against the surface region of the abrasive means, the leading edge of the crowns will be chamfered, beveled or deburred.

An inside surface region of the scaffold can be processed to shape the luminal surface regions of the crowns, struts and other scaffold structures by inserting a flexible abrasive means through the interior of the scaffold.

Ink jet printing technologies can also be used to build up some portions of the scaffold or the scaffold to achieve concave luminal and abluminal surface regions and convex side surface regions of the scaffold structures. As an example, a dispenser nozzle (or ink jet print head or cartridge or reservoir therefor) may be filled with a polymeric material solution or an extrusion nozzle loaded with a solid rod of the polymeric material. The nozzle may then be positioned close to the surface region of an object such as a mandrel (optionally substantially round mandrel, preferably a 3-D patterned mandrel of the stent pattern desired) providing a former which together with control of the dispenser nozzle enables material to be deposited onto the mandrel to form a stent embodying the invention. For example, the mandrel may have approximately the deployed or optionally larger than the intended deployed diameter of the stent (labeled or nominal) or optionally 1.1-1.5 times larger than intended deployed diameter of the stent, and optionally the mandrel may have the inner (luminal) surface region shape of the stent and the dispenser nozzle may be controlled to dispense or extrude the polymer as the mandrel is rotated. In addition, the nozzle or the mandrel can be moved radially and or axially by a 3-axis motion controller. The polymer may be dispensed or extruded from the nozzle in a preprogrammed scaffold pattern and the dispensing of the polymer be controlled to vary the shape of surface regions to provide straight, concave and/or convex shaped surface regions as describes throughout this application. For example, one or more layers or traces of polymeric material can be laid down on top of each other to achieve a certain structural elements thickness. Also, the width of the layer or trace may be adjusted, to make it narrower. The nozzle may then dispenses or extrudes the polymeric material along one side of the initial trace and then repeat for the other side to achieve an abluminal concave surface region and the sides of the struts forming a convex surface region. The scaffold may be either left to dry, vacuumed, heat set, left to cool, or the like, or a combination thereof. Afterwards, the scaffold may be removed from the mandrel by swelling the scaffold with solvent such as ethanol, acetone, tetrahydrofuran, methylene chloride, or the like, or a combination thereof. After removal, the scaffold can be left to dry, vacuumed, heat set, left to cool, or the like, or a combination thereof. The scaffold may or may not be coated with a polymer-drug matrix, crimped on a delivery balloon catheter, packaged, and sterilized.

It should be appreciated that the stent structural elements or the stent itself may be manufactured so that the required surface regions have the required shape. As an example, the stent structural elements or the stent itself may be manufactured by way of '3D printing' whereby a three-dimensional model of the stent structural elements or the stent itself is supplied, in machine readable form, to a '3D printer' adapted to manufacture the stent structural elements or the stent itself. This may be by additive means such as extrusion, deposition, Electron Beam Freeform Fabrication (EBF), granular materials binding, lamination, photopolymerization, or stereolithography or a combination thereof or by a removal process such as ablation or cutting. The machine readable model may comprise a spatial map of the object to be printed, typically in the form of a Cartesian coordinate system defining the object's surface regions. This spatial map may comprise a computer file which may be provided in any one of a number of file conventions. One example of a file convention is a STL (STereoLithography) file which may be in the form of ASCII (American Standard Code for Information Interchange) or binary and specifies areas by way of triangulated surface regions with defined normals and vertices. Another file format is AMF (Additive Manufacturing File) which provides the facility to specify the material and texture of each surface region as well as allowing for curved triangulated surface regions. The mapping of the stent structural elements or the stent itself may then be converted into instructions to be executed by 3D printer according to the printing method being used. This may comprise splitting the model into slices (for example, each slice corresponding to an x-y plane, with successive layers building the z dimension) and encoding each slice into a series of instructions. The instructions sent to the 3D printer may comprise Numerical Control (NC) or Computer NC (CNC) instructions, preferably in the form of G-code (also called RS-274), which comprises a series of instructions regarding how the 3D printer should act. The instructions vary depending on the type of 3D printer being used, but in the example of a moving printhead the instructions include: how the printhead should move, when/where to deposit material, the type of material to be deposited, and the flow rate of the deposited material.

The stent structural elements or the stent itself as described herein may be embodied in one such machine readable model, for example a machine readable map or instructions, for example to enable a physical representation of said stent structural elements or the stent itself to be produced by 3D printing. This may be in the form of a software code mapping of the strut and/or crown and/or instructions to be supplied to a 3D printer (for example numerical code).

Molding, over molding or compression of a preformed part in a shaped mold can also be used to form the scaffold with the shaped concave luminal and abluminal surface regions and convex side surface regions of the scaffold structures or to treat a scaffold to form the concave luminal and abluminal surface regions and convex side surface regions.

5. Laser Shaping

A laser can be used to shape the scaffold structures. With a laser having the ability to ablate with low energy and layer by layer, such as a femtosecond laser, a laser cutting program can be set to ablate a desired shape of the scaffold surface regions. In one example, the laser can be used to create concave luminal and abluminal surface regions and convex side surface regions of the scaffold structures. A series of laser formed steps can create the convex side surface regions of the struts. In a similar manner, the laser can be used to create the concave luminal or flat or concave abluminal surface regions by a series of small steps along the surface region. The steps can be smoothed out with solvent, sandblasting, tumbling, or the like.

In one example, a series of overlapping cuts, with each cut narrower than 35 micrometers, narrower than 30 micrometers, or narrower than 25 micrometers can be made from the abluminal surface region to the side surface region of the scaffold structure to achieve the convex side surface region on the crown, axial strut or other scaffold structure.

In another example, the scaffold can be cut during the laser cutting process with off-axis control such that the axis of the laser beam and the axis of the assist gas supply nozzle on the laser such as a femtosecond laser is eccentrically oriented. This allows the laser to cut material at an angle rather than straight cut, resulting in a curved surface region. This process can be used to form the curved surface regions described herein.

The convex side surface regions of the scaffold can also be formed using either trepanning or helical drilling. Trepanning is a combined cutting and drilling process, typically performed using a pulsed laser. In trepanning, a through hole is first pierced by percussion drilling and then in a second step the through hole is widened to its final diameter in a circular cutting motion by the laser. In a similar manner, the laser beam can cut the material at an angle to form the curved surface regions. After a first cut at an angle to form the rounded top portion of the strut side surface regions, the laser can cut the rest of the scaffold pattern with a straight cut. This results in a partially convex side surface region. It is also possible to make the last part of the laser at an angle so that side surface region is fully convex. In helical drilling, a rotational movement of the laser beam is used to create a positive or negative taper at the scaffold surface regions.

6. Heat Shaping

In another example, the surface regions of scaffold can be melted by thermal energy and the material can be redistributed to achieve the desired shaping of the surface regions. In the thermal method heat may be applied in an oven, for a duration and at a temperature to provide convex side surface regions and/or concave luminal and abluminal surface regions. The heating temperature can be controlled to reach the melting temperature of the polymer at the surface regions to be shaped without reaching the melting temperature in the remainder of the scaffold material.

It should be appreciated that the required shape may be formed by adding material to the surface region of the original stent structural element, removing from the surface region of the original stent structural element and/or moving material on the surface region of the original stent structural element.

The amount of material added, moved and/or removed will be determined based on the original shape of the surface region of the stent structural element and the required shape of the surface region of the stent structural element. Material may be removed from the outer edge, added to the central portion, moved from the outer edge to the central portion, and/or moved from the outer edge to an adjacent side of the stent structural element to form a convex surface region. Material may be removed from the central portion, added to the outer edge, moved from the central portion to the outer edge, and/or moved from an adjacent side to the outer edge of the stent structural element to form a concave surface region.

It should be appreciated that various techniques may be used to remove material from the structural elements so that the required surface regions have a concave and/or a convex shape. For example, material can be removed from the surface region of a strut using techniques such as negative '3D printing', nanofabrication, microfabrication, photolithography, lithography, and etching.

The stent structural element may also be manufactured to the required shape. For example, the stent structural element may be extruded such that the profile of the stent structural element has the required shape. In a further example the stent prosthesis may be manufactured with stent structural elements of the required shape using a molding process.

The convex side surface regions can also improve flexibility of the scaffold or stent. The scaffold with curved axial struts can bend in a multitude of directions compared to axial struts with flat surface regions. For example, a scaffold with rectangular axial struts or links will bend primarily in two preferred directions because of the flat surface regions of the axial struts. The struts cannot bend in the direction of the edge. However, modified strut cross sections with convex sides provide more freedom to bend in multiple directions and thus provide a more flexible and deliverable stent or scaffold.

When the struts, crowns and/or other scaffold structures are coated with a drug for delivery to a lumen, convex side surface regions can provide for a more uniform drug coating and thus can release drug from a substantially more uniform surface region than a square or rectangular strut. Concave luminal and abluminal surface regions also can provide improved directionality of drug delivery to the lumen or vessel wall.

For a substantially amorphous polymer material which is less than 15%, preferably less than 10% crystalline, solvent shaping of the tubular body does not significantly alter the crystalline orientation of the material since the substantially amorphous material is random in crystalline orientation.

Figure 12:
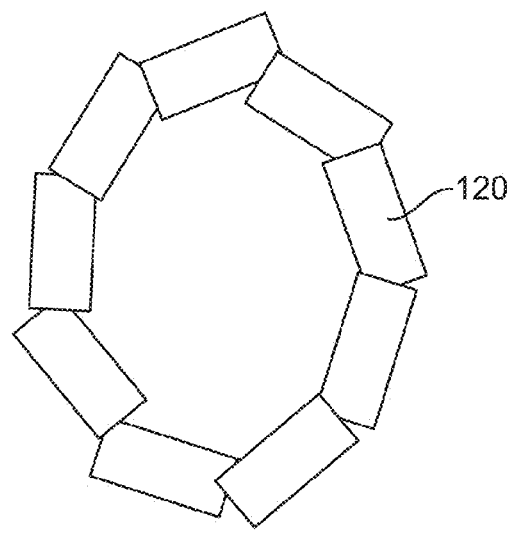
FIG. 12 is a cross section of a crimped stent having unmodified side surface regions.
Figure 13:
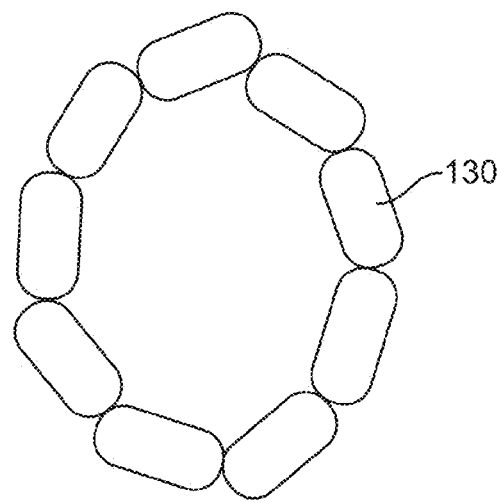
FIG. 13 is a cross section of a crimped stent having modified side surface regions.

Convex side surface regions can also improve crimping of the scaffold or stent because convex structure sides are more resistant to overlapping struts when crimped from a larger as-cut diameter to a smaller crimped diameter due to the absence of flat surface regions which can catch on one another during crimping. FIG. 12 illustrates an end view of a crimped stent with rectangular cross section stent structural elements 120. The rectangular stent structural elements 120 can overlap and twist due to crimping. The stent structural elements 130 of FIG. 13 having curved side surface regions can reduce or eliminate the overlapping and twisting which occurs with flat rectangular surface regions. FIG. 13 shows a stent body in cross section with convex side surface regions of the stent structural elements. Twisting and rotating of stent structural elements along their axis can happen during expansion as well as during crimping. The convex side surface regions and concave abluminal surface regions prevent or reduce rotating of stent structural elements during crimping and/or during expansion to less than 45 degrees, less than 35 degrees or less than 25 degrees.

Struts or other scaffold structures having shaped surface regions as described above can be considered to have oblong, oval, elliptical, near elliptical, circular, near circular, or dogbone like cross sectional shapes. Where the shaping treatment is performed before application of the drug in a preferred embodiment, the drug coating process achieves a product with shaped surface regions as the coating process maintains substantially the same shape.

In one embodiment, the biodegradable stent prosthesis comprises a body having a plurality of rings each ring comprises a plurality of struts joined by crowns, wherein each ring is connected to an adjacent ring by at least one link.

In another embodiment, the biodegradable stent prosthesis comprises a body having a plurality of struts joined by crowns.

In yet another embodiment, the biodegradable stent prosthesis comprises a body having a plurality of rings connected by at least one link, and a plurality struts joined by crowns.

In another example, the biodegradable stent prosthesis comprises a body having abluminal surface regions, luminal surface regions, and two side surface regions of each structural component of the stent, along the length of the stent.

In another embodiment, the biodegradable stent prosthesis comprises a polymeric material forming a tubular body, wherein said body comprises a stent pattern having a plurality of struts, crowns and optionally links, each having four surface regions, such that a cross section of said struts is rectangular having a concave abluminal surface region and/or convex side surface region, and a cross section of said crown is substantially rectangular having convex side surface regions and/or optionally a concave abluminal surface region. The cross-section is substantially rectangular in the sense that the dimensions of width and thickness are different.

Although rectangular and square cross sections having four sides are described other cross sections have more than four sides or fewer than four sides are also contemplated.

In another embodiment, the biodegradable stent prosthesis comprises a polymeric material forming a tubular body, wherein said body comprises a stent pattern having a plurality of struts, crowns and optionally links, each having four surface regions, such that a cross section of said struts is substantially square having concave abluminal surface regions, and/or convex side surface regions, and a cross section of said crown is substantially square having convex side surface regions, and/or optionally concave abluminal surface region. The cross-section is substantially square in the sense that the dimensions of width and thickness are substantially the same.

The biodegradable stent prosthesis may be expandable from a crimped configuration to an expanded larger configuration to support a body lumen or a blood vessel.

The biodegradable stent prosthesis may be expandable from a crimped configuration to an expandable larger configuration at body temperature.

The biodegradable stent prosthesis may be expandable from a crimped configuration to an expandable larger configuration and have sufficient strength to support a body lumen or a blood vessel.

The biodegradable stent prosthesis may be circumferentially expandable from a crimped configuration to an expanded larger configuration.

In some embodiments, the biodegradable stent prosthesis comprises a biodegradable polymeric material.

In other embodiments, the biodegradable stent prosthesis comprises a biodegradable metal or metal alloy.

In other embodiments, the biodegradable stent prosthesis comprises a biodegradable polymeric material, and a biodegradable metal or metal alloy.

In other embodiments, the biodegradable prosthesis comprises a degradable polymeric material, said polymeric material is formed as a tubular body using extrusion, dipping, spraying, or printing.

In some embodiments, the biodegradable stent prosthesis comprises a degradable metal or metal alloy, said metal or metal alloy is formed as a tubular body.

In one embodiment, an expandable biodegradable prosthesis comprises an expandable prosthesis body formed from a biodegradable polymeric material, the expandable prosthesis body having a plurality of stent structural elements each having luminal and abluminal surface regions. The plurality of stent structural elements includes a plurality of circumferentially expandable serpentine rings, each serpentine ring including axial struts joined by crowns. At least some of the abluminal surface regions are concave across substantially the width of the stent structural elements. The prosthesis is expandable from a crimped configuration to an expanded larger configuration to support a body lumen.

In another embodiment, the biodegradable stent prosthesis comprises a degradable polymeric material formed as a tubular body, said stent is patterned into a structure comprising a plurality of rings, wherein each ring comprises a plurality of struts and crowns, wherein adjacent rings are connected by at least one link, wherein the stent struts have abluminal and luminal surface regions, wherein at least some of the struts abluminal surface regions are concave across substantially the width of said struts.

In another embodiment, the biodegradable stent prosthesis comprises a degradable polymeric material formed as a tubular body, said stent is patterned into a structure comprising a plurality of rings, wherein each ring comprises a plurality of struts and crowns, wherein adjacent rings are connected by at least one link, wherein the stent struts have abluminal and luminal surface regions, wherein substantially all of the struts abluminal surface regions are concave across substantially the width of said struts.

In another embodiment, the biodegradable stent prosthesis comprises a degradable polymeric material formed as a tubular body, said stent is patterned into a structure comprising a plurality of rings, wherein each ring comprises a plurality of struts and crowns, wherein adjacent rings are connected by at least one link, wherein the stent struts have abluminal and luminal surface regions, and at least one side surface region between the luminal and abluminal surface regions, wherein at least some of the struts abluminal surface regions are concave across substantially the width of said struts, and wherein at least some of the struts side surface regions are convex across substantially the thickness of said struts.

In one embodiment, the biodegradable stent prosthesis is patterned into a structure comprising a plurality of serpentine rings, each ring comprises struts joined by crowns, and wherein adjacent rings are joined by at least one link, said rings have abluminal and luminal surface regions, and two side surface regions between the luminal and abluminal surface regions; wherein at least some of the rings luminal surface regions are concave across substantially the width of said ring, and wherein at least some of the rings side surface regions are convex across substantially the thickness of said ring.

In some embodiments, the stent structural elements comprise side surface regions extending between the luminal and abluminal surface regions, wherein at least some of the side surface regions are convex.

In some embodiments, the expandable prosthesis body is formed from a tube and the formed prosthesis body has been treated to form the concave abluminal surface regions.

In some embodiments, the expandable prosthesis body is formed from a flat sheet and the formed prosthesis body has been treated to form the concave luminal and abluminal surface regions.

In some embodiments, the treatment does not substantially change the weight or mass of the prosthesis body.

In some embodiments, the stent prosthesis is treated to form concave shapes across substantially the width of the stent abluminal surface regions, and convex shapes across substantially the thickness of the stent side surface regions, wherein the weight or mass of the stent prosthesis before treatment and after treatment is substantially the same.

In some embodiments, the stent prosthesis is treated to form concave shapes across substantially the width of the stent abluminal surface regions, and convex shapes across substantially the thickness of the stent side surface regions, wherein the weight or mass of the stent prosthesis before treatment and after treatment are within 15% of each other.

In some embodiments, the stent prosthesis is formed comprising concave shapes across substantially the width of the stent abluminal surface regions, and convex shapes across substantially the thickness of the stent side surface regions, and wherein the weight or mass of the stent prosthesis before treatment and after treatment is substantially the same.

In one embodiment, a method of forming an expandable polymer prosthesis with modified surface regions includes the steps of forming a tubular expandable prosthesis with a plurality of stent structural elements each having a luminal surface region, an abluminal surface region and two side surface regions extending between said luminal and abluminal surface regions by patterning the prosthesis from a polymer tube; and exposing the expandable prosthesis to a treatment for a predetermined period of time to modify the surface regions, wherein resulting modified abluminal surface regions are concave.

In some embodiments of the method the modified side surface regions of the expandable prosthesis are convex.

In some embodiments of the method the treatment changes the shapes of the surface regions and does not substantially change the weight or mass of the prosthesis.

In one embodiment, an expandable prosthesis includes an expandable prosthesis body formed from a plurality of stent structural elements including struts, crowns and optionally links, each having luminal and abluminal surface regions and side surface regions extending between the luminal and abluminal surface regions, wherein at least some of the abluminal surface regions are concave and wherein at least some of the side surface regions are convex, wherein said prosthesis is expandable from a crimped configuration to an expanded larger configuration to support a body lumen.

In some embodiments, the endoprosthesis is patterned from a tube by laser cutting and the laser cut treatment forms the concave abluminal surface regions and convex side surface regions. In some embodiments, the treatment comprises shaping by application of a solvent by at least one of dipping, spraying, or contact with a solvent vapor.

In some embodiments, the treatment includes shaping by tumbling, agitating, deburring, scraping, or sandblasting. In a further example, the processing includes shaping with a laser or heat. The processing can be followed by forming a coating of at least one drug formed over the expandable endoprosthesis body.

In another example, the endoprosthesis comprises a plurality of circumferentially expandable serpentine rings, each serpentine ring comprises axial struts joined by crowns, wherein one crown joins two adjacent axial struts of a serpentine ring, and wherein the crowns act as hinges allowing the struts to spread as the ring expands circumferentially, at least one link joining adjacent serpentine rings.

The stent endoprosthesis may be formed from a biodegradable polymeric material which has a molecular weight ranging from 100 KDa to 1000 KDa. In another embodiment, the biodegradable polymeric material has an elastic modulus of at least 0.35 Gpa, preferably between 0.35 Gpa and 1.5 Gpa.

The biodegradable polymeric material may comprise one or more of polymers and copolymers. The endoprosthesis may be capable of being expanded from a crimped diameter to a deployed diameter at body temperature without fracture of the endoprosthesis.

The endoprosthesis may comprise a biodegradable polymeric material comprising one or more of: Lactide, poly- DL-Lactide, polylactide-co-glycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

In other embodiments, the polymeric material comprises one or more polymers or copolymers, or polymer blends.

The prosthesis body may be formed as a tube and patterned by laser cutting.

The endoprosthesis is preferably balloon expandable.

In other embodiments, the endoprosthesis is self-expandable.

In other embodiments, the stent prosthesis is self-expandable and balloon expandable.

In an embodiment, a polymer endoprosthesis comprises a tubular expandable endoprosthesis body comprising a polymeric material which has been patterned from a tube to form the stent, said stent comprises a plurality of stent structural elements each stent structural element having a luminal surface region, an abluminal surface region, and two side surface regions extending between said luminal and abluminal surface regions, wherein at least one of the abluminal surface regions is concave, and wherein the two side surface regions are convex.

A drug coating comprising at least one drug may be coated on at least a portion of the expandable endoprosthesis body. The at least one drug may be contained within a coating, preferably a polymeric coating, covering at least a portion of the stent prosthesis.

In an embodiment, a method of forming a polymer endoprosthesis prosthesis with modified surface regions comprises the steps of forming a tubular expandable endoprosthesis with a plurality of stent structural elements each having a luminal surface region, an abluminal surface region and two side surface regions extending between said luminal and abluminal surface regions by cutting the endoprosthesis from a polymer tube and exposing the tubular expandable endoprosthesis to a treatment for a predetermined period of time to modify the surface regions, wherein the resulting modified abluminal surface regions are concave while the modified two side surface regions are convex.

In some embodiments, at least some of the abluminal surface regions of some portions of the polymeric prosthesis are concave and at least some of the side surface regions are concave.

In another embodiment substantially all of the abluminal surface regions of the prosthesis are concave and substantially all of the side surface regions of the prosthesis are convex.

The treatment may change the shapes of the surface regions and not substantially change the weight or mass of the endoprosthesis.

The treatment process may not significantly dissolve the polymeric material from which the endoprosthesis is formed.

The treatment process may not substantially dissolve the polymeric material from which the endoprosthesis is formed.

In another method, the treatment does not dissolve more than 10%, more than 15% or more than 20% of the polymeric material from which the endoprosthesis is formed.

In another method, the treatment does not substantially degrade the polymeric material from which the endoprosthesis is formed either mechanically or chemically.

Preferably, the treatment shifts polymeric material from at least one surface region to an adjacent surface region without a substantial change in weight or mass before and after treatment.

Preferably, the treatment shifts polymeric material from at least one surface region to an adjacent surface region modifying at least some abluminal surface regions into concave shape and at least some side surface regions into convex surface regions without a substantially change in the weight or mass before and after treatment.

The treatment may shift polymeric material from abluminal and/or luminal surface regions of the stent prosthesis to the side surface regions of the stent prosthesis (or vice versa), preferably without substantially loss of material, more preferably without weight or mass change of more than 5%, most preferably without substantial change in stent weight or mass.

The treatment may shift polymeric material from at least one side surface region to one of luminal or abluminal surface regions of the stent prosthesis, preferably without substantially loss of material, more preferably without loss of more than 5%, most preferably without substantial change in stent weight or mass.

In a further embodiment, a method of forming a polymer endoprosthesis prosthesis with a controlled strut thickness includes the steps of forming a tubular expandable endoprosthesis with a plurality of struts by cutting the endoprosthesis from a polymer tube having a first thickness, said endoprosthesis comprising a polymeric material and exposing the tubular expandable endoprosthesis to a solvent for a predetermined period of time to redistribute said polymeric material without substantially dissolving it to adjust a thickness of the plurality of struts to a second thickness, wherein the second thickness is greater than the first thickness.

In another embodiment, a polymer endoprosthesis includes a tubular expandable endoprosthesis body comprising a polymeric material which has been cut from a tube to form an endoprosthesis with a plurality of stent structural elements each having a luminal surface region, an abluminal surface region, and two side surface regions extending between said luminal and abluminal surface regions, wherein the two side surface regions are convex and have a radius of curvature of at least 0.020 mm.

In a further embodiment, a polymer endoprosthesis comprises a tubular expandable endoprosthesis body comprising a polymeric material which has been cut from a tube to form an endoprosthesis with a plurality of stent structural elements each having a luminal surface region, an abluminal surface region, and two side surface regions extending between said luminal and abluminal surface regions, wherein the abluminal surface regions of the stent structural elements are shaped to form concave surface regions extending substantially from one side surface region to an opposite side surface region; a coating comprising at least one drug formed over the tubular expandable endoprosthesis body. Preferably, a coating comprising a drug is coated over said abluminal surface region without substantially changing the concave shape.

In another embodiment, a method of forming a polymer endoprosthesis prosthesis with a modified shape includes the steps of forming a tubular expandable endoprosthesis with a plurality of stent structural elements having luminal, abluminal and side surface regions extending between said luminal and abluminal surface regions by cutting the endoprosthesis from a polymer tube having a first thickness and treating the tubular expandable endoprosthesis to increase a thickness of the plurality of stent structural elements between the luminal and abluminal surface regions while decreasing a width of the stent structural elements between the side surface regions by redistributing the polymer. Preferably, the treating increases the thickness of a plurality of stent structural elements but the width of the stent structural elements remains unchanged. The width and thickness may be measured as the maximum dimensions for the width and thickness, taken at the widest or thickest spot on the strut. Although the maximum dimensions can be used, the minimum, median, average or mean dimensions, or whatever is appropriate in the circumstances can be used for dimensions. The changes or no changes can be detected regardless of the measurement protocol selected.

In another embodiment, the biodegradable stent prosthesis comprises a biodegradable polymeric material formed as a tubular body, wherein said tubular body is composed of an abluminal surface region, a luminal surface region, and two side surface regions, wherein the tubular body is patterned into a structure having an abluminal surface region, a luminal surface region, and side surface regions, and wherein the stent is treated after patterning to shift polymeric material from at least one side surface region to said luminal and/or abluminal surface regions.

In another embodiment, the biodegradable stent prosthesis comprises a biodegradable polymeric material formed as a tubular body, wherein said tubular body is composed of an abluminal surface region, a luminal surface region, and at least two side surface regions, wherein the tubular body is patterned into a structure having an abluminal surface region, a luminal surface region, and at least two side surface regions, and wherein the stent is treated after patterning to shift polymeric material from at least some luminal and/or abluminal surface regions to at least one adjacent side surface region, wherein the at least said treated abluminal surface regions become substantially concave, and wherein the at least adjacent side surface regions become substantially convex.

In another embodiment, the biodegradable stent prosthesis comprises a biodegradable polymeric material formed as a tubular body, wherein said tubular body is composed of an abluminal surface region, a luminal surface region, and at least two side surface regions, wherein the tubular body is patterned into a structure having an abluminal surface region, a luminal surface region, and at least two side surface regions, and wherein the stent is treated after patterning to shift polymeric material from at least some side surface regions to at least one adjacent luminal and/or abluminal surface region (or vice versa shifting material from luminal and/or abluminal to side), wherein the at least some treated abluminal surface regions become substantially concave, and wherein the at least some adjacent side surface regions become substantially convex, and wherein the weight or mass of the stent prosthesis before and after said treatment is substantially the same.

In another embodiment, the biodegradable stent prosthesis comprises a biodegradable polymeric material formed as a substantially flat body, wherein said body is composed of an abluminal surface region, a luminal surface region, and at least two side surface regions, wherein the body is patterned into a structure having an abluminal surface region, a luminal surface region, and at least two side surface regions, and wherein the stent is treated after patterning to shift polymeric material from at least some side surface regions to at least on adjacent luminal and/or abluminal surface region, wherein the at least said treated luminal and/or abluminal surface regions become substantially concave, and wherein the at least adjacent side surface regions become substantially convex, and wherein the weight or mass of the stent prosthesis before and after said treatment is substantially the same.

The surface region roughness of treated luminal, abluminal, and adjacent sides may be substantially reduced after treatment. For example, the surface region roughness of treated luminal, abluminal, and adjacent side surface regions, may be substantially reduced after process treatment. In an example, the root-mean-square roughness (Sq) ranges between 0.5 micrometers to 15 micrometers. In another example the roughness average (Sa) ranges from 0.5 micrometers to 10 micrometers as measured by optical profilometry or atomic force microscopy.

The treated surface regions may increase crystallinity at the surface region of the stent prosthesis by at least 15%.

The treated surface region may have a crystallinity that is substantially different from the core of the treated stent prosthesis by at least 15%, or by at least 20%, or by at least 25%, or by at least 30%. The crystallinity of the treated surface region within 25% depth from the treated surface region may be substantially different from the crystallinity of the said core of the treated stent prosthesis.

The treatment may increase cross linking at the surface region of the stent prosthesis. Increased cross linking results in a scaffold which absorbs less solvent when exposed to the solvent. The increase in cross linking results in absorption of solvent reduction by at least 10%.

The treated stent prosthesis surface region may have an increased hydrophobicity. This is very helpful when coating the stent prosthesis with a coating or a drug comprising a solvent wherein the absorption of said solvent is reduced by at least 10%. It can also be helpful to delay substantially complete hydration of the stent prosthesis by at least 1 minute.

When fabricating a biodegradable stent prosthesis, it is desirable to design the prosthesis such that the stent design comprising stent structural elements, for example crowns or/and struts, having width to thickness dimensions that are approximately 1:1, or range from approximately 0.8:1 to approximately 1.1:1, such that upon expansion of the biodegradable stent prosthesis said stent structural elements along the length of the stent prosthesis are substantially free from rotating around their axis, or substantially free from rotating more than 45 degrees around their axis. This allows the stent prosthesis to have improved strength such as sufficient strength to support a body lumen, improved uniformity of expansion, and/or be free from fracture upon expanding the stent from a crimped configuration to an expanded larger configuration.

However, such desire is difficult to achieve when using biodegradable material since the biodegradable material are typically weaker material and therefore in order to achieve smaller thickness, the width of such stent prosthesis stent structural elements, for example struts, will be larger than thickness, typically width to thickness ratio are at least 1.2:1, and that contributes to having stent structural elements along the length of the stent prosthesis prone to rotating or twisting upon expanding the stent prosthesis from a crimped configuration to an expanded larger configuration, resulting in lower strength, lower uniformity of expansion, or strut and/or crown fracture, upon expansion of the stent or after expansion. It is therefore desirable to be able to design a biodegradable stent prosthesis that is smaller in thickness, having a width to thickness ratio of at least 1.2:1 wherein the stent structural elements upon expansion or after expansion are substantially free from said stent structural elements rotating, or substantially free from rotating more than 45 degrees around their axis, or substantially free from rotating more than 25 degrees around their axis. Such desire for performance is achieved when fabricating a stent comprising stent structural elements that have at least some of the luminal and/or abluminal surface region concave, and optionally at least some of the sides extending between said luminal and abluminal surface regions convex, said degradable stent prosthesis stent structural elements upon expansion from crimped configuration to an expanded configuration are substantially free from rotating more than 45 degrees around their axis.

In an embodiment, the biodegradable stent prosthesis comprises a biodegradable polymeric material formed as a tubular body using extrusion, dipping, spraying or printing, wherein the stent prosthesis is patterned into a structure comprising stent structural elements, such as struts, wherein said stent structural elements having widths that are at least 1.2 times said stent structural element thickness, wherein the patterned structure comprises luminal, abluminal, and side surface regions, wherein at least some of said stent structural elements having concave abluminal surface regions along the width of said stent structural elements, and optionally wherein at least some of said stent structural elements have at least one convex side surface region extending between said abluminal and luminal surface region, said stent prosthesis is expandable from a crimped configuration to an expanded larger configuration wherein the said stent structural elements remain substantially free from rotating.

In one embodiment, an expandable prosthesis includes an expandable prosthesis body formed from a plurality of stent structural elements each having luminal and abluminal surface regions and side surface regions extending between the luminal and abluminal surface regions, wherein at least some of the luminal and abluminal surface regions are concave and wherein at least some of the side surface regions are convex, wherein said prosthesis is expandable from a crimped configuration to an expanded larger configuration to support a body lumen.

The endoprosthesis may be cut from a tube by laser cutting and the laser cut prosthesis has been processed to form the concave luminal and abluminal surface regions and convex side surface regions. In another example the processing includes shaping by application of a solvent by at least one of dipping, spraying, or contact with a solvent vapor.

The endoprosthesis stent structural elements can include a plurality of circumferentially expandable serpentine rings, each serpentine ring including struts joined by crowns, wherein one strut joins two adjacent crowns of a serpentine ring, and wherein the crowns act as hinges allowing the struts to spread as the ring expands circumferentially, links joining some but not all crowns on adjacent serpentine rings. The treatment may modify the surface regions of all of the scaffold structures of the endoprosthesis.

In another embodiment, a polymer endoprosthesis includes a tubular expandable endoprosthesis body comprising a polymeric material which has been cut from a tube to form an endoprosthesis with a plurality of struts each having a luminal surface region, an abluminal surface region, and two side surface regions extending between said luminal and abluminal surface regions, wherein at least one of the luminal and abluminal surface regions is concave and the two side surface regions are convex In another embodiment, a method of forming a polymer endoprosthesis with modified surface regions includes the steps of forming a tubular expandable endoprosthesis with a plurality of struts each having a luminal surface region, an abluminal surface region and two side surface regions extending between said luminal and abluminal surface regions by cutting the endoprosthesis from a polymer tube and exposing the tubular expandable endoprosthesis to a treatment for a predetermined period of time to modify the surface regions, wherein the resulting modified luminal and abluminal surface regions are concave while the modified two side surface regions are convex.

The Tg of the polymer comprised in the polymeric scaffold after the shaping process may be substantially unchanged from before the treatment process.

The crystallinity of the polymer comprised in the polymeric scaffold after the shaping process may be substantially unchanged from before the treatment process.

The molecular weight of the polymer comprised in the polymeric scaffold after the shaping process may be substantially unchanged from before the treatment process.

The molecular number of the polymer comprised in the polymeric scaffold after the shaping process may be substantially unchanged from before the treatment process.

In the polydispersity index of the polymer comprised in the polymeric scaffold after the shaping process may be substantially unchanged from before the treatment process.

In a further embodiment, a method of forming a polymer stent prosthesis with a controlled strut thickness includes the steps of forming a tubular expandable prosthesis with a plurality of struts by cutting the prosthesis from a polymer tube having a first thickness, said prosthesis comprising a polymeric material and exposing the tubular expandable prosthesis to a solvent for a predetermined period of time to redistribute said polymeric material without substantially dissolving it to adjust a thickness of the plurality of struts to a second thickness, wherein the second thickness is greater than the first thickness.

In a further embodiment, a polymer endoprosthesis includes a tubular expandable endoprosthesis body comprising a polymeric material which has been cut from a tube to form an endoprosthesis with a plurality of struts each having a luminal surface region, an abluminal surface region, and two side surface regions extending between said luminal and abluminal surface regions, wherein the abluminal surface regions of the struts are shaped to form concave surface regions extending substantially from one side surface region to an opposite side surface region; and a coating comprising at least one drug formed over at least some portions of the tubular expandable endoprosthesis body. The at least one drug may coat all surface regions of the tubular expandable endoprosthesis body.

In another embodiment, a method of forming a polymer stent prosthesis with a modified shape includes the steps of forming a tubular expandable prosthesis with a plurality of struts having luminal, abluminal and side surface regions extending between said luminal and abluminal surface regions by cutting the prosthesis from a polymer tube having a first thickness and treating the tubular expandable endoprosthesis to increase a thickness of the plurality of struts between the luminal and abluminal surface regions while decreasing a width of the struts between the side surface regions by redistributing the polymer.

In one embodiment, the biodegradable stent prosthesis comprises a tubular biodegradable polymeric material, said polymeric material is patterned into a stent capable of radial expansion from a crimped diameter to a deployed larger diameter, wherein the stent comprises a plurality of struts joined by crowns and at least some of the crowns are connected to adjacent crowns, wherein said patterned stent struts and crowns, each have a luminal surface region, an abluminal surface region, and two side surface regions extending between said luminal and abluminal surface regions, wherein at least some abluminal surface regions (optionally substantially all abluminal surface regions) have concave shapes across substantially the width of said abluminal surface regions, and at least some side surface regions (optionally substantially all side surface regions) have convex shapes across the thickness of said side surface regions, wherein the stent in the deployed diameter has sufficient strength to support a blood vessel.

In one embodiment, the biodegradable polymeric stent prosthesis comprises a tubular biodegradable polymeric material, said polymeric material is patterned into a stent capable of radial expansion from a crimped diameter to a deployed larger diameter, wherein the stent comprises a plurality of struts joined by crowns and at least some of the crowns are connected to adjacent crowns, wherein said patterned stent struts and crowns each have a luminal surface region, an abluminal surface region, and two side surface regions extending between said luminal and abluminal surface regions, wherein at least some abluminal surface regions (optionally substantially all abluminal surface regions) have concave shapes across substantially the width of said abluminal surface regions, and at least some side surface regions (optionally substantially all side surface regions) have convex shapes across the thickness of said side surface regions, wherein the stent in the deployed diameter has sufficient strength to support a blood vessel.

In one embodiment, the biodegradable polymeric stent prosthesis comprises a tubular biodegradable polymeric material, said polymeric material is patterned into a stent body capable of radial expansion from a crimped diameter to a deployed larger diameter, wherein the stent body comprises a plurality of struts joined by crowns and at least some of the crowns are connected to adjacent crowns, wherein said patterned stent structural elements each have a luminal surface region, an abluminal surface region, and two side surface regions extending between said luminal and abluminal surface regions, wherein at least some abluminal surface regions (optionally substantially all abluminal surface regions) have concave shapes across substantially the width of said abluminal surface regions, and at least some side surface regions (optionally substantially all side surface regions) have convex shapes across the thickness of said side surface regions, wherein the stent body in the deployed diameter has sufficient strength to support a blood vessel.

In one embodiment, the biodegradable stent prosthesis comprises a tubular biodegradable polymeric material, said polymeric material has a stent pattern, said stent capable of radial expansion from a crimped diameter to a deployed larger diameter, wherein the stent comprises a plurality of struts joined by crowns and at least some of the crowns are connected to adjacent crowns, wherein said stent struts and crowns each have a luminal surface region, an abluminal surface region, and two side surface regions extending between said luminal and abluminal surface regions, wherein at least some abluminal surface regions (optionally substantially all abluminal surface regions) have concave shapes across substantially the width of said abluminal surface regions, and at least some side surface regions (optionally substantially all side surface regions) have convex shapes across the thickness of said side surface regions, wherein the stent in the deployed diameter has sufficient strength to support a blood vessel.

In one embodiment, the biodegradable polymeric stent prosthesis comprises a tubular biodegradable polymeric material, said polymeric material is patterned into a stent capable of radial expansion from a crimped diameter to a deployed larger diameter, wherein the stent comprises a plurality of struts joined by crowns and at least some of the crowns are connected to adjacent crowns, wherein said patterned stent structural elements each have a luminal surface region, an abluminal surface region, and two side surface regions extending between said luminal and abluminal surface regions, wherein at least some abluminal surface regions (optionally substantially all abluminal surface regions) have concave shapes, and at least some side surface regions (optionally substantially all side surface regions) have convex shapes, wherein the stent in the deployed diameter has sufficient strength to support a blood vessel.

In one embodiment, the biodegradable stent prosthesis, comprising a biodegradable polymeric material, said polymeric material is patterned into a stent capable of expansion from a crimped diameter to a deployed larger diameter, wherein the patterned stent comprises a plurality of struts, crowns, and optionally links connecting at least some adjacent crowns, wherein said patterned stent struts, crowns, and links each have a luminal surface region, an abluminal surface region, and two side surface regions extending between said luminal and abluminal surface regions, wherein at least some abluminal surface regions (optionally substantially all abluminal surface regions) have concave shapes across substantially the width of said abluminal surface regions, and at least some side surface regions (optionally substantially all side surface regions) have convex shapes across the thickness of said side surface regions, wherein the patterned stent in the deployed diameter has sufficient strength to support a blood vessel. The polymeric material may be formed as a tubular body.

In one embodiment, the biodegradable stent prosthesis comprises a biodegradable polymeric material, said polymeric material is patterned into a stent capable of expansion from a crimped diameter to a deployed larger diameter, wherein the patterned stent comprises a plurality of struts, crowns, and optionally links connecting at least some adjacent crowns, wherein said patterned stent struts, crowns, and links each have a luminal surface region, an abluminal surface region, and two side surface regions extending between said luminal and abluminal surface regions, wherein at least some abluminal surface regions (optionally substantially all abluminal surface regions) have concave shapes along substantially the width of said abluminal surface regions, and at least some side surface regions (optionally substantially all side surface regions) have convex shapes along the thickness of said side surface regions, wherein the patterned stent in the deployed diameter has sufficient strength to support a blood vessel. The polymeric material may be formed as a tubular body.

In one embodiment, the biodegradable polymeric stent prosthesis comprises a biodegradable polymeric material, said polymeric material formed as a tubular body and patterned into a stent capable of expansion from a crimped diameter to a deployed larger diameter, wherein the patterned stent comprises a plurality of struts joined by crowns wherein at least some adjacent crowns are connected, wherein said patterned stent struts and crowns, each have a luminal surface region, an abluminal surface region, and two side surface regions extending between said luminal and abluminal surface regions, wherein at least some abluminal surface regions are (optionally substantially all abluminal surface regions) have concave shapes across substantially the width of said abluminal surface regions, and at least some side surface regions (optionally substantially all side surface regions) have convex shapes across the thickness of said side surface regions, wherein the patterned stent in the deployed diameter has sufficient strength to support a blood vessel.

The concave abluminal surface regions and convex side surface regions, may substantially increase the surface region area along the length of stent prosthesis, while reducing surface region porosity of the luminal and side surface regions.

The concave abluminal surface regions and convex side surface regions, may substantially increase the surface region area along the length of stent prosthesis, while substantially maintaining surface region porosity of the luminal and side surface regions.

The patterned stent may expand from a crimped configuration to a larger expanded configuration substantially free from rotation of patterned stent struts, crowns, and optionally links.

The patterned stent may expand from a crimped configuration to a larger expanded configuration having rotation of patterned stent struts, crowns, and optionally links, less than 45 degrees.

In one embodiment, the biodegradable stent prosthesis, comprises a biodegradable polymeric material, said polymeric material is patterned into a stent capable of radial expansion from a crimped diameter to a deployed larger diameter, wherein the patterned stent comprises a plurality of struts joined by crowns wherein at least some adjacent crowns are connected, wherein said patterned stent struts and crowns each have a luminal surface region, an abluminal surface region, and two side surface regions extending between said luminal and abluminal surface regions, wherein the patterned stent is treated and at least some abluminal surface regions (optionally substantially all abluminal surface regions) are modified from being substantially convex shapes to become flat or have a concave shape across substantially the width of said abluminal surface regions, and at least some side surface regions (optionally substantially all side surface regions) are modified from being substantially flat shapes to substantially convex shapes across the thickness of said side surface regions, wherein the patterned stent in the deployed diameter has sufficient strength to support a blood vessel.

In one embodiment, the biodegradable stent prosthesis, comprises a biodegradable polymeric material, said polymeric material is patterned into a stent capable of expansion from a crimped diameter to a deployed larger diameter, wherein the patterned stent comprises a plurality of struts joined by crowns wherein at least some adjacent crowns are connected, wherein said patterned stent struts and crowns each have a luminal surface region, an abluminal surface region, and two side surface regions extending between said luminal and abluminal surface regions, wherein the patterned stent is treated and at least some side surface regions (optionally substantially all side surface regions) are modified from being substantially flat shapes to substantially convex shapes across the thickness of said side surface regions, wherein the patterned stent in the deployed diameter has sufficient strength to support a blood vessel.

The polymeric material may be formed from a tubular body.

The biodegradable prosthesis may be a polymeric biodegradable prosthesis.

In one embodiment, the biodegradable polymeric stent prosthesis, comprises a biodegradable polymeric material, said polymeric material is patterned into a stent capable of radial expansion from a crimped diameter to a deployed larger diameter, wherein the patterned stent comprises a plurality of struts joined by crowns wherein at least some adjacent crowns are connected, wherein said patterned stent struts and crowns each have a luminal surface region, an abluminal surface region, and two side surface regions extending between said luminal and abluminal surface regions, wherein the patterned stent is treated and at least some side surface regions (optionally substantially all side surface regions) are modified to substantially convex shapes across the thickness of said side surface regions, wherein the patterned stent in the deployed diameter has sufficient strength to support a blood vessel.

In one embodiment, the biodegradable polymeric stent prosthesis comprises a biodegradable polymeric material, said polymeric material formed as a tubular body and patterned into a stent capable of expansion from a crimped diameter to a deployed larger diameter, wherein the patterned stent comprises a plurality of struts joined by crowns wherein at least some adjacent crowns are connected, wherein said patterned stent struts and crowns each have a luminal surface region, an abluminal surface region, and two side surface regions extending between said luminal and abluminal surface regions, wherein the patterned stent is treated and at least some abluminal surface regions (optionally substantially all abluminal surface regions) are modified to substantially concave shapes across substantially the width of said abluminal surface regions, and at least some side surface regions (optionally substantially all side surface regions) are modified to substantially convex shapes across the thickness of said side surface regions, wherein the patterned stent in the deployed diameter has sufficient strength to support a blood vessel.

The treatment of the stent prosthesis to modify the abluminal surface regions to concave shapes and the side surface regions to convex shapes may allow the polymeric material to flow from one surface region to an adjacent surface region.

The treatment of the stent prosthesis to modify the abluminal surface regions to concave shapes and the side surface regions to convex shapes may allow the polymeric material to flow from one surface region to an adjacent surface region without substantially dissolving the polymeric material.

The treatment of the stent prosthesis to modify the abluminal surface regions to concave shapes and side surface regions to convex shapes may allow the polymeric material to flow from one surface region to an adjacent surface region, without substantially changing the stent pattern.

The treatment of the stent prosthesis to modify the abluminal surface regions to concave shapes and the side surface regions to convex shapes may increase hydrophobicity of said surface regions, preferably by at least 15%, more preferably by at least 30%, most preferably by at least 50%.

The treatment of the stent prosthesis to modify the abluminal surface regions to concave shapes and the side surface regions to convex shapes may allow the polymeric material to flow from one surface region to an adjacent surface region.

The treatment of the stent prosthesis to modify the abluminal surface regions to concave shapes and the side surface regions to convex shapes may prevent said surface regions from rotating around their axis upon expansion of the stent prosthesis from a crimped configuration to an expanded larger configuration to support a blood vessel.

The treatment of the stent prosthesis to modify the abluminal surface regions to concave shapes and the side surface regions to convex shapes may allow the polymeric material to flow from one surface region to an adjacent surface region, without substantially changing the weight or mass of the stent prosthesis.

The biodegradable stent prosthesis may be a polymeric biodegradable stent prosthesis. As an example, the biodegradable polymeric stent prosthesis may be substantially all comprised of polymeric material. In another example, the polymeric biodegradable stent prosthesis is substantially all comprised of polymeric material and metallic radiopaque markers. In another example, the polymeric biodegradable stent prosthesis is substantially all comprised of polymeric material and non-polymeric radiopaque markers. In another example, the polymeric biodegradable stent prosthesis is substantially all comprised of polymeric material and some non-polymeric material.

In one embodiment, the treatment of the stent prosthesis to modify the abluminal surface regions to concave shapes or to a concave shape provides abluminal surface regions having a concave shape, but not necessarily identical concave shapes. Similarly, the treatment of the stent prosthesis to modify the side surface regions to convex shapes or to a convex shape provides side surface regions having a convex shape but not necessarily identical convex shapes. The resulting shapes may vary in radii of curvature and where on the strut, crown or link the midpoint of the curve occurs.

The polymeric degradable stent may be formed from a tubular body by extrusion, dipping, spraying, or printing, wherein the tubular body is formed and patterned at 1.1 to 1.5 times an intended deployed diameter of the stent (labeled nominal diameter), and treating the patterned stent to form concave shapes on at least some abluminal surface regions of the struts and crowns, and convex shapes on at least some side surface regions of said struts and crowns. The stent prosthesis may then be coated with a drug and polymer matrix maintaining the concave abluminal surface regions and convex side surface regions, may then be crimped onto a delivery system, packaged, and sterilized. Optionally the tube or stent is heated at a temperature ranging between 50 degrees and 150 degrees Celsius for between 1 minute and 5 hours, before patterning and/or after patterning, one or more times.

EXAMPLES

Example 1

Biodegradable polymer scaffolds made from polylactide based polymer were treated with a solvent of 4 parts dichloromethane (methylene chloride) and 6 parts ethanol for 5 seconds and rinsed with ethanol for 3 seconds. Both treated and non-treated scaffolds were then heat treated for 3 hours at 90 deg. C. They were coated with a drug matrix coating and sterilized by Ebeam. The scaffolds were tested for radial strength using an Instron connected to an iris based tester. Treated and untreated scaffolds were chosen based on their similarity in thickness and width to show the benefits of treatment in increasing strength for the same or similar strut profile. As shown in Table 1, the radial strength of the treated scaffolds with modified structure cross section of convex sides and concave luminal and abluminal surface region were higher by at least 15% than the similarly sized scaffolds with substantially rectangular struts (non-treated).

TABLE 1

Summary of Radial Strength

| | Strut Thickness | | Strut Width | | Radial Strength | |
|---|---|---|---|---|---|---|
| | inches | micrometer | In | micrometer | (psi) | n |
| Treated | 0.0043 | 110 | 0.0074 | 188 | 13.7 | 3 |
| Non-Treated | 0.0046 | 116 | 0.0074 | 188 | 11.9 | 4 |

FIG. 2 shows a cross section of a scaffold strut after treatment. The scaffold cross section before treatment had substantially rectangular laser cut struts. The scaffold of FIG. 2 is shown before coating with drug matrix.

The strut after treatment has a narrower width and a slightly greater thickness as shown in Table 2 below.

TABLE 2

Summary of Dimension Changes with Treatment

| | Strut Thickness | | Strut Width | |
|---|---|---|---|---|
| | Inches | micrometers | Inches | micrometers |
| Before Treatment | 0.0032 | 81 | 0.0080 | 203 |
| After Treatment | 0.0043 | 116 | 0.0074 | 188 |

For the particular treatment process in this Example, the struts after treatment have convex side surface regions and have a slight concavity in the luminal and abluminal surface regions. The strut dimensions given in Table 2 are maximum dimensions for the width and thickness, taken at the widest or thickest spot on the strut. According to this example, the treatment resulted in a 43% increase in strut thickness and a 7% decrease in strut width.

A percent shape modification treatment, or amount of change in shape, can be calculated by measuring at one cross section the minimum strut width, generally at the luminal or abluminal surface region of the strut $_{(Wmin)}$ and the maximum strut width $_{(Wmax)}$ which occurs near a midpoint between the luminal or abluminal surface region of the strut and calculating percent treatment=$[1-(W_{min}-W_{max})] \times 100$ as shown in Table 3. In one example, the percent shape modification treatment is at least 10%, or at least 20%, or at least 30% or at least 40%.

TABLE 3

PercentTreatment

| | Ring 1 Strut Width (in) | | Middle Ring Strut Width (in) | |
|---|---|---|---|---|
| Unit # | Max | Min | Max | Min* |
| 3 × 28 mm | | | | |
| 1 | 0.0073 | 0.0035 | 0.0075 | 0.0048 |
| 2 | 0.0073 | 0.0043 | 0.0074 | 0.0045 |
| 3 | 0.0073 | 0.0044 | 0.0071 | 0.0045 |
| 4 | 0.0074 | 0.0042 | 0.0073 | 0.0041 |
| 5 | 0.0072 | 0.0045 | 0.0068 | 0.0031 |
| Average | 0.0073 | 0.0042 | 0.0072 | 0.0042 |
| Low | 0.0072 | 0.0035 | 0.0068 | 0.0031 |
| High | 0.0074 | 0.0045 | 0.0075 | 0.0048 |
| % shape modification Treatment | | | 43% | |

TABLE 3-continued

| | Percent Treatment | | | |
|---|---|---|---|---|
| | Ring 1 Strut Width (in) | | Middle Ring Strut Width (in) | |
| Unit # | Max | Min | Max | Min* |
| 3 × 14 mm | | | | |
| 1 | 0.0071 | 0.0045 | 0.0071 | 0.0044 |
| 2 | 0.0071 | 0.0047 | 0.0069 | 0.0046 |
| 3 | 0.0078 | 0.0048 | | |
| Average | 0.0074 | 0.0047 | 0.0070 | 0.0045 |
| Low | 0.0071 | 0.0045 | 0.0069 | 0.0044 |
| High | 0.0078 | 0.0048 | 0.0071 | 0.0046 |
| | % Treatment | | 37% | |

The treated scaffolds of Example 1 were found to have no significant weight/mass change after treatment. This shows that the solvent is not removing polymer from the scaffolds, but is instead redistributing the polymer material to modify the shape of the surface regions. In this example, the difference in mass before and after treatment is less than 1%.

TABLE 4

Mass Before and After Treatment

| Before shape modification Treatment (mg) | |
|---|---|
| 1 | 5.212 |
| 2 | 5.309 |
| 3 | 5.337 |
| Mean | 5.286 |
| After shape modification Treatment (mg) | |
| 1 | 5.194 |
| 2 | 5.353 |
| 3 | 5.370 |
| 4 | 5.379 |
| 5 | 5.372 |
| Mean | 5.329 |
| % Difference | 0.81% |

Example 2

In another example, the side and abluminal surface regions of at least a portion of the struts, crowns, links and other scaffold structures can be shaped by solvent dipping while maintaining a substantially flat surface region on the luminal side by inserting a tight mandrel such as a Teflon rod or tube inside the scaffold. The scaffold supported tightly on the mandrel is then dipped into a first solvent for about 1 second, 2 seconds, 3 seconds, or up to 20 seconds to cause the solvent to redistribute polymer material. The scaffold is quickly removed from the solvent when the desired shaping is achieved. Preferably the scaffold is rinsed in a second solvent to remove materials that are adhering to the scaffold and to fix the desired shape. FIG. 4 shows a cross sectional shape of a scaffold which can result from treatment by this process.

Although a tight fitting inner mandrel is described for blocking contact of the first solvent with the luminal side of the scaffold, other methods of masking the luminal side can also be used to prevent shaping of the luminal surface regions of the scaffold. Although the luminal surface region of the scaffold without treatment are described as substantially flat surface regions, it should be understood that the scaffold if formed from a tube, have surface regions with some slight curvature corresponding to the curvature of the tube. Substantially flat surface regions can occur if the structure is formed from a sheet.

Example 3

Biodegradable polymer scaffolds made from polylactide based polymer were treated with a solvent based scaffold modification process described above to provide a structure cross section with convex sides and concave abluminal surface region. The modification of the scaffold surface region shapes was to provide improved tracking and/or push by reducing the force required to track or push the scaffold mounted on a catheter through a cylindrical body, such as a blood vessel. The reduction of track or push force is achieved by changing the area of surface region contact between the modified scaffold shape and the vessel. On the abluminal side, the unmodified surface regions on the scaffold structure can act like ratchet elements as the scaffold is pushed through a blood vessel, especially one with calcified lesions. This may inhibit tracking through the vessel because the sides may get caught on the walls of the artery.

A test method was developed to characterize a force required for a scaffold delivery system to cross a lesion located at the apex of a curve in a test fixture with a curved track to simulate a blood vessel.

Figure 14:
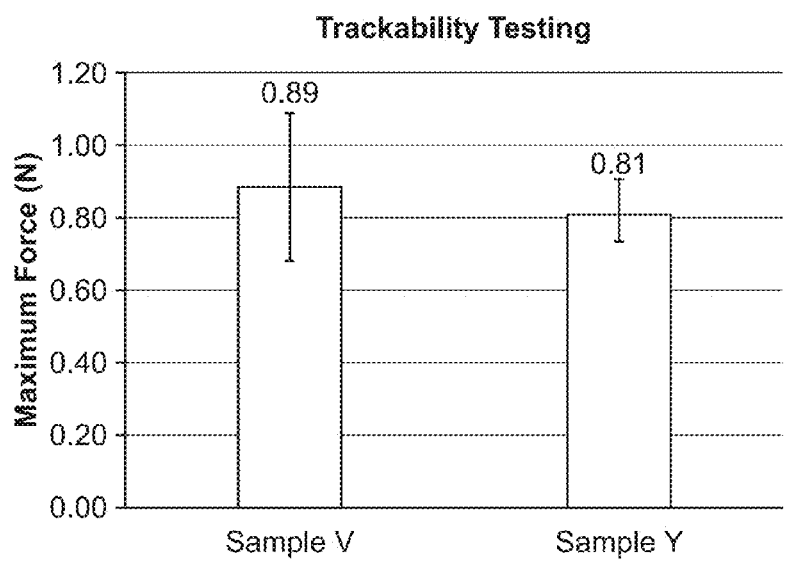
FIG. 14 is a graph of the results of trackability testing.

The fixture is immersed in a water bath maintained at 37° C. and the catheter with a mounted scaffold is pushed through the fixture. The push force is measured by the Instron attached to the catheter delivery system. The force is measured for units with scaffolds with no modification (sample V) and flat side surface regions and scaffolds with shape modification with convex side structures (sample Y). FIG. 14 shows a lower push force for the modified scaffold, indicating better trackability.

Example 4

A bioresorbable scaffold of 6.0 mm diameter and 60 mm in length is laser cut from a tube of 200 micrometer thickness made from a copolymer of polylactic acid-co-glycolide. The scaffold is mounted on a smaller mandrel rotating around its longer axis in an enclosed refrigerated chamber and is exposed to surface region modification with dry ice blasting equipment. The sandblasting nozzle is attached to a programmable robotic arm to propel particles along the selected portions of the scaffold crowns and axial struts. The dry ice blasting nozzle is aimed at the luminal surface regions to compact the treated surface region and create the concave shape of these surface regions. The nozzle of the equipment is aimed at the corners at an angle of about 20 to about 160 degrees with respect to the strut side surface regions to achieve compaction of material at the side surface regions at the corners to provide convex side surface regions without removing significant amounts of material from other parts of the scaffold. As described herein, the scaffold can be either tightly mounted on a mandrel or loosely mounting on a mandrel depending on the location of the surface regions to be shaped. The scaffold can also be positioned inside a tube to shape at least a portion of the surface regions on the luminal surface region of the scaffold.

Example 5

Figure 15:
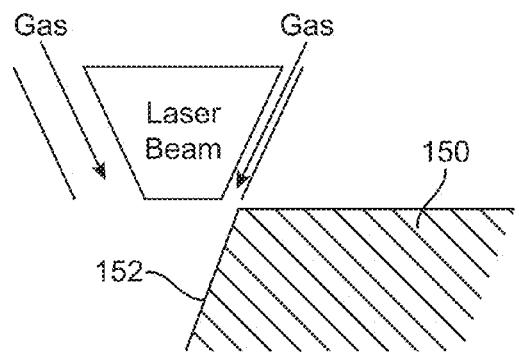
FIG. 15 is a schematic illustration of a laser process for creating convex side surface regions.

A bioresorbable scaffold of 3.5 mm diameter and 28 mm in length is laser cut from a tube of 100 micrometer thickness made from a polymer of polylactic acid based copolymer. A femtosecond laser is used to create convex and concave surface region crowns on a scaffold. Because of the ability to ablate with low energy and cut layer by layer, a laser cutting program can be set to ablate about 25 or smaller micrometer width slots. As shown in FIG. 15, a series of overlapping cuts are made from the top surface region to the edge of the scaffold structure 150 to achieve the desired shape on the crown, axial strut, or link. The scaffold structure can be cut with off-axis control such that the axis of laser beam and the axis of the assist gas supply nozzle on the laser such as a femtosecond laser is eccentrically oriented. This allows the laser to cut the scaffold material at an angle 152 rather than straight cut, eventually resulting in the convex cross section side surface regions.

Figure 16:
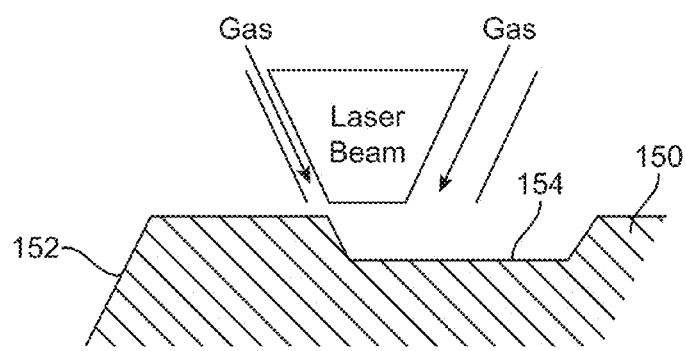
FIG. 16 is a schematic illustration of a laser process for creating concave luminal or abluminal surface regions.

FIG. 16 shows the process of the laser being used to create a concave surface region on the luminal and/or abluminal surface regions by ablating the mid-section of the crown, strut or link 150 in stepwise cuts 154 in the surface region of 150 to eventually create a concavity across substantially the width of the crown, strut or link.

Example 6

A multi-piece metal mold is created with fine scaffold negative features using wire EDM with the desired shaped strut features having convex sides and concave luminal and abluminal surface regions and held together under high pressure with holding clamps.

The equipment used is specifically designed to mold microparts with small plastic shot sizes for example a 3.5 mm×28 mm scaffold of 13 cubic millimeters, by utilizing high pressure of up to 100,000 psi and high speed to achieve injection times of around 0.01 seconds, to decrease the dwell time in the mold and minimize thermal degradation of the polymer. The strut width is 200 um and thickness is 200 um.

PLA based polymer is heated in the plasticizing portion of the machine, to the melt temperature of 200° C., and fed into the mold portion of the machine by the injector plunger.

After injection the mold is cooled rapidly to freeze the molten plastic and minimize thermal degradation, and the part removed. The scaffold structure has a cross section with the convex side surface regions and concave luminal and abluminal surface regions.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions; wherein at least some of the abluminal surface regions are concave across substantially the width of the surface, optionally at least some of the side surface regions are convex across substantially the width of the surface.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions; wherein at least some of the abluminal surface regions have a concave overall surface shape, optionally at least some of the side surface regions have a convex overall surface shape, where the overall shape of a surface region is defined as the shape of a curve fitted to the actual surface by an appropriate fitting procedure such as a least squares fitting procedure.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions; wherein at least some of the side surface regions are convex across substantially the width of the surface and at least some of the abluminal surface regions are flat or concave across substantially the width of the surface.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions; wherein at least some of the side surface regions have a convex overall surface shape and at least some of the abluminal surface regions have a concave or flat overall surface shape, where the overall shape of a surface region is defined as the shape of a curve fitted to the actual surface by an appropriate fitting procedure such as a least squares fitting procedure.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the width varies across the thickness.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the width varies across the thickness such that the width increases in a direction away from the luminal and abluminal surface regions.

Embodiments of the disclosure provide an biodegradable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the width varies across the thickness such that a minimum width is at the luminal and abluminal surface regions.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the thickness varies across the width.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the thickness varies across the width such that thickness decreases in a direction away from the side surface regions.

Embodiments of the disclosure provide an expandable stent prosthesis comprising: a tubular expandable stent prosthesis body, said tubular expandable stent prosthesis body comprising stent structural elements each having a luminal surface region, an abluminal surface region and side surface regions coupling the luminal and abluminal surface regions, the stent structural element having a thickness between the luminal and abluminal surface regions and a width between the side surface regions; wherein for at least some of the stent structural elements the width varies across the thickness such that a minimum width is at the luminal and abluminal surface regions.

Embodiments of the disclosure provide an expandable stent prosthesis that preferably is biodegradable.

In embodiments of the disclosure, the tubular expandable stent prosthesis body may comprise a non-braided tubular body. For example, the tubular expandable stent prosthesis body may comprise a patterned tubular body. The patterned tubular body may be patterned by cutting or etching, for example by use of a laser. As examples the tube may be formed by extrusion, spraying, dipping or molding. The tubular expandable stent prosthesis body may be formed as a tube or from a flat sheet which may be patterned before or after being formed into a cylinder to form the tubular body. Any of these tubular bodies may be pre-formed with the above-described surface shapes or may be modified after formation to provide the above-described surface shapes. Where a tubular body is formed from a flat sheet then the flat sheet may be pre-formed with the above-described surface shapes or may be modified after formation to provide the above-described surface shapes.

In embodiments, concave abluminal surface regions can provide benefits in drug coating and in drug delivery and benefits in embedding the stent prosthesis into the vessel wall. In embodiments, a reduction of tracking or push force required to track or push a stent mounted on a catheter through a cylindrical body, such as a blood vessel, may be achieved because of the change of the area of contact between the stent prosthesis and the vessel wall resulting from the surface region shaping. In embodiments, a lower push force may be required for stent prostheses with convex side surface regions than for stent prostheses with flat side surface regions, providing better trackability.

Throughout the specification, including the claims, where the context permits, the term "comprising" and variants thereof such as "comprises" or "comprising" are to be interpreted as including the stated integer or integers without necessarily excluding any other integers.

The Disclosure of this Application Also Includes the Following Numbered Clauses:

1. An expandable biodegradable stent prosthesis comprising:

a tubular expandable stent prosthesis body comprising a biodegradable material, said expandable stent prosthesis body comprising stent structural elements having luminal and abluminal surface regions; wherein at least some of the abluminal surface regions have a concave shape across substantially the width of said surface regions.

In embodiments of the disclosure, a concave abluminal surface region minimizes or at least reduces the possibility of slippage of the stent prosthesis when expanded to a deployed configuration, such that the stent structural elements hug the vessel wall or the plaque area better.

In embodiments of the disclosure, concave abluminal surface regions may prevent or reduce rotating of stent structural elements during crimping and/or during expansion.

In embodiments of the disclosure, concave luminal and/or abluminal surface regions may also provide improved directionality of drug delivery to the lumen or vessel wall.

2. The expandable biodegradable stent prosthesis of clause 1, wherein said stent structural elements each have side surface regions extending between the luminal and abluminal surface regions; and wherein at least some of the side surface regions have a convex shape across substantially the thickness of said stent structural elements.

3. The expandable biodegradable stent prosthesis of clause 2 or 3, wherein substantially all of the side surface regions have a convex shape across substantially the thickness of said side surface regions.

In embodiments of the disclosure, concave abluminal surface regions and convex side surface regions, may increase the surface region area along the length of stent prosthesis, while reducing or maintaining surface region porosity of the luminal and side surface regions.

4. The expandable biodegradable stent prosthesis of clause 1, wherein said stent structural elements each have side surface regions extending between the luminal and abluminal surface regions; and wherein at least some of the side surface regions have a concave shape across substantially the thickness of said stent structural elements.

5. The expandable biodegradable stent prosthesis of clause 4, wherein substantially all of the side surface regions have a concave shape across substantially the thickness of said side surface regions.

6. The expandable biodegradable stent prosthesis of any of clauses 1 to 5, wherein substantially all of the abluminal surface regions have a concave shape across substantially their width.

7. The expandable biodegradable stent prosthesis of any of clauses 1 to 6, wherein at least some of the luminal surface regions have a concave shape across substantially the width of said surface regions.

8. The expandable biodegradable stent prosthesis of clause 7, wherein substantially all of the luminal surface regions have a concave shape across substantially their width.

9. An expandable biodegradable stent prosthesis comprising:

a tubular expandable stent prosthesis body, said expandable stent prosthesis body comprising stent structural elements each having a surface with a luminal surface region, an abluminal surface region, coupling portions coupling the abluminal and luminal surface regions, and a thickness between said luminal and abluminal surface regions; wherein at least a part of at least some of the coupling portions is bulbous.

10. The expandable stent prosthesis of clause 9, wherein the abluminal surface region is flat.

11. The expandable stent prosthesis of clause 9, wherein the abluminal surface region is concave.

12. The expandable stent prosthesis of clause 9, 10 or 11, wherein the luminal surface region is flat.

13. The expandable stent prosthesis of clause 9, 10 or 11, wherein the luminal surface region is flat.

14. The expandable stent prosthesis of any of clauses 9 to 13, wherein the surface has two side surface regions each coupling the abluminal and luminal surface regions and the side surface regions comprise bulbous coupling portions.

15. The expandable stent prosthesis of any of clauses 9 to 13, wherein the surface has two side surface regions each coupling the abluminal and luminal surface regions and there are two bulbous coupling portions each defined by the abluminal surface region and a respective one of the side surface regions.

16. The expandable stent prosthesis of any of clauses 9 to 13, wherein the surface has two side surface regions each coupling the abluminal and luminal surface regions and there are two bulbous coupling portions each defined by the luminal surface region and a respective one of the side surface regions.

17. The expandable stent prosthesis of any of clauses 9 to 13, wherein the surface has two side surface regions each coupling the abluminal and luminal surface regions and there are four bulbous coupling portions two defined by the luminal surface region and the side surface regions and two defined by the luminal surface region and the side surface regions.

18. The expandable stent prosthesis of clause 9, wherein the surface has a dogbone or dumbbell shape with two opposed end bulbous coupling portions.

19. The expandable stent prosthesis of clause 9, wherein the surface has two side surface regions each coupling the abluminal and luminal surface regions and there are two bulbous coupling portions each defined by the abluminal surface region and a respective one of the side surface regions, wherein the abluminal surface region has a concave portion.

20. The expandable stent prosthesis of clause 9, wherein the surface has two side surface regions each coupling the abluminal and luminal surface regions and there are two bulbous coupling portions each defined by the abluminal surface region and a respective one of the side surface regions, wherein the abluminal surface region has a concave portion, the side regions are flat and the luminal surface region is flat or convex.

21. The expandable prosthesis of any of clauses 2 to 8, wherein the stent structural elements each have two side surface regions extending between the luminal and abluminal surface regions.

22. The expandable stent prosthesis of any of clauses 1 to 21, wherein the stent structural elements comprise struts and crowns.

23. The expandable stent prosthesis of clause 22, wherein the stent prosthesis body comprises expandable rings, each ring is composed of struts joined by crowns, and each ring is connected to an adjacent ring by at least one link.

24. The expandable stent prosthesis of any of clauses 1 to 23 wherein said surface region shape is formed by treating the expandable stent prosthesis.

25. The expandable stent prosthesis of clause 24, wherein the treatment includes shaping by application of a solvent by at least one of dipping, spraying, or contact with a solvent vapor.

26. The expandable stent prosthesis of clause 24 or 25, wherein the treatment includes shaping by tumbling, agitating, deburring, scraping, media blasting, laser treatment or heat treatment.

27. The expandable stent prosthesis of clause 24, 25 or 26, wherein a weight of the expandable stent prosthesis after treatment is substantially the same as before treatment.

28. The expandable stent prosthesis of any of clauses 24 to 27, wherein the treatment does not significantly dissolve the polymeric material from which said prosthesis is formed.

29. The expandable stent prosthesis of any of clauses 24 to 28 wherein the treatment shifts material from a surface region of a said stent structural element to an immediately adjacent surface region of a said stent structural element without a substantial change in body weight of said expandable stent prosthesis.

30. The expandable stent prosthesis of any of clauses 24 to 29, said body has been treated to adjust a thickness of stent structural elements from a first thickness before treatment to a second thickness after treatment, wherein the second thickness is greater than the first thickness.

31. The expandable stent prosthesis of any of clauses 24 to 30, wherein the treatment causes a thickness of stent structural elements between the luminal and abluminal surface regions to increase while a width of the stent structural elements between the side surface regions remains substantially the same.

32. The expandable stent prosthesis of any of clauses 24 to 31, wherein the treatment causes a thickness of stent structural elements between the luminal and abluminal surface regions to increase while decreasing a minimum width of the stent structural elements between the side surface regions by redistributing the biodegradable material.

33. The expandable stent prosthesis of any of clauses 24 to 32, wherein the treatment comprises exposing the expandable stent prosthesis to a solvent for a predetermined period of time.

34. The expandable stent prosthesis of any of clauses 1 to 33, wherein the expandable stent prosthesis body has been patterned from a tube by a laser.

35. The expandable stent prosthesis of any of clauses 1 to 34, further comprising a coating formed over at least some portions of the expandable stent prosthesis body.

36. The expandable stent prosthesis of clause 35, wherein surface region shape is retained after coating.

37. The expandable stent prosthesis of clause 35 or 36 wherein the coating comprises a drug.

38. The expandable stent prosthesis of any of clauses 1 to 37, wherein the biodegradable material comprises biodegradable polymeric material.

39. The expandable stent prosthesis of clause 38, wherein the biodegradable polymeric material comprises at least one material selected from the group consisting of lactides, poly-DL-Lactide, polylactide-co-glycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

40. The expandable stent prosthesis of clause 38 or 39, wherein the biodegradable polymeric material of said expandable stent prosthesis body comprises at least two biodegradable polymers.

41. The expandable prosthesis of clause 38, 39 or 40, wherein the biodegradable polymeric material has an elastic modulus of at least 0.35 GPa.

42. The expandable stent prosthesis of clause 38 or 39, wherein the biodegradable polymeric material comprises one or more of polymers and copolymers.

43. The expandable stent prosthesis of any of clauses 38 to 42, wherein the biodegradable polymeric material has a molecular weight ranging from 100 KDa to 1000 KDa.

44. The expandable stent prosthesis of any of clauses 1 to 43, wherein the prosthesis is balloon expandable.

45. An expandable biodegradable stent prosthesis comprising:
a tubular expandable stent prosthesis body, which may comprise a biodegradable material, such as a biodegradable polymeric material, wherein the stent comprises a plurality of stent structural elements, wherein said structural elements each have a luminal surface region, an abluminal surface region, and two side surface regions extending between the luminal and abluminal surface regions; and wherein at least some of the side surface regions have a convex shape.

In embodiments of the disclosure, the surface region area over which the tensile and compressive stresses are distributed during bending of a stent structural element is increased due to the convex side surface regions and this leads to increased radial strength of the stent prosthesis.

In embodiments of the disclosure, convex side surface regions enable greater contact than square or rectangular flat surface regions between balloon material of the delivery system and the stent prosthesis. For example, in a process of crimping the stent prosthesis onto a balloon, there may be an increased surface region area of contact between the stent structural element with convex side regions and a flap of the balloon than with the flat side surface regions which may enable improved scaffold retention on a balloon catheter in a crimped configuration. Convex side surface regions can also improve crimping of the stent prosthesis because convex side surface regions are more resistant to overlapping or twisting which may occur with flat rectangular surface regions during expansion and/or during crimping.

In embodiments of the disclosure, convex side surface regions can also improve flexibility of the stent prosthesis. For example, a stent structural element scaffold with convex side surface regions may be able to bend in more directions than to a stent structural element with flat surface regions providing a more flexible and deliverable stent prosthesis.

In embodiments of the disclosure, when stent structural elements are coated with a drug for delivery to a lumen, convex side surface regions can provide for a more uniform drug coating and thus can release drug from a substantially more uniform surface region than a square or rectangular strut.

46. The expandable biodegradable stent prosthesis of clause 45, wherein at least some of the abluminal surface regions have a concave shape or are flat across substantially the width of said abluminal surface regions.

47. The expandable biodegradable stent prosthesis of clause 45 or 46, wherein substantially all of the side surface regions have a convex shape across substantially the thickness of said side surface regions.

48. The expandable biodegradable stent prosthesis of clause 45, 46 or 47, wherein said prosthesis has been treated by contact with a solvent to redistribute said biodegradable material to provide said surface region shape.

49. The expandable biodegradable stent prosthesis of clause 45, 46, 47 or 48, wherein said prosthesis has been treated by contact with a solvent to redistribute said biodegradable material to provide an increased thickness of said side surface regions and decreased width of said abluminal and luminal surface regions.

50. The expandable biodegradable stent prosthesis of any of clauses 45 to 49, wherein substantially all of the abluminal surface regions have a concave shape across substantially their width.

51. The expandable biodegradable stent prosthesis of any of clauses 45 to 50, wherein at least some of the luminal surface regions have a concave shape across substantially the width of said surface regions.

52. The expandable biodegradable stent prosthesis of any of clauses 45 to 50, wherein at least some of the luminal surface regions are flat across substantially the width of said surface regions.

53. The expandable biodegradable stent prosthesis of any of clauses 45 to 50, wherein at least some of the luminal surface regions have a concave shape across substantially the width of said surface regions.

54. The expandable stent prosthesis of any of clauses 45 to 53, wherein the stent structural elements comprise struts and crowns.

55. The expandable stent prosthesis of clause 54, wherein the stent prosthesis body comprises expandable rings, each ring is composed of struts joined by crowns, and each ring is connected to an adjacent ring by at least one link.

56. The expandable stent prosthesis of any of clauses 45 to 55 wherein said surface region shape is formed by treating the expandable stent prosthesis.

57. The expandable stent prosthesis of clause 56, wherein the treatment includes shaping by application of a solvent by at least one of dipping, spraying, or contact with a solvent vapor.

58. The expandable stent prosthesis of clause 46 or 47, wherein the treatment includes shaping by tumbling, agitating, deburring, scraping, media blasting, laser treatment or heat treatment.

59. The expandable stent prosthesis of clause 56, 57 or 58, wherein a weight of the expandable stent prosthesis after treatment is substantially the same as before treatment.

60. The expandable stent prosthesis of any of clauses 45 to 59, wherein the treatment does not significantly dissolve the polymeric material from which said prosthesis is formed.

61. The expandable stent prosthesis of any of clauses 45 to 60 wherein the treatment shifts material from a surface region of a said stent structural element to an immediately adjacent surface region of a said stent structural element without a substantial change in body weight of said expandable stent prosthesis.

62. The expandable stent prosthesis of any of clauses 45 to 61, said body has been treated to adjust a thickness of stent structural elements from a first thickness before treatment to a second thickness after treatment, wherein the second thickness is greater than the first thickness.

63. The expandable stent prosthesis of any of clauses 45 to 62, wherein the treatment causes a thickness of stent structural elements between the luminal and abluminal surface regions to increase while a width of the stent structural elements between the side surface regions remains substantially the same.

64. The expandable stent prosthesis of any of clauses 45 to 62, wherein the treatment causes a thickness of stent structural elements between the luminal and abluminal surface regions to increase while decreasing a minimum width of the stent structural elements between the side surface regions by redistributing the biodegradable material.

65. The expandable stent prosthesis of any of clauses 45 to 64, wherein the treatment comprises exposing the expandable stent prosthesis to a solvent for a predetermined period of time.

66. The expandable stent prosthesis of any of clauses 45 to 65, wherein the expandable stent prosthesis body has been patterned from a tube by a laser.

67. The expandable stent prosthesis of any of clauses 45 to 66, further comprising a coating formed over at least some portions of the expandable stent prosthesis body.

68. The expandable stent prosthesis of clause 67, wherein surface region shape is retained after coating.

69. The expandable stent prosthesis of clause 67 or 68 wherein the coating comprises a drug.

70. The expandable stent prosthesis of any of clauses 45 to 69, wherein the biodegradable material comprises biodegradable polymeric material.

71. The expandable stent prosthesis of clause 70, wherein the biodegradable polymeric material comprises at least one material selected from the group consisting of lactides, poly-DL-Lactide, polylactide-co-glycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

72. The expandable stent prosthesis of clause 70 or 71, wherein the biodegradable polymeric material of said expandable stent prosthesis body comprises at least two biodegradable polymers.

73. The expandable prosthesis of clause 70, 71 or 72, wherein the biodegradable polymeric material has an elastic modulus of at least 0.35 GPa.

74. The expandable stent prosthesis of clause 70 or 73, wherein the biodegradable polymeric material comprises one or more of polymers and copolymers.

75. The expandable stent prosthesis of any of clauses 70 to 74, wherein the biodegradable polymeric material has a molecular weight ranging from 100 KDa to 1000 KDa.

76. The expandable stent prosthesis of any of clauses 45 to 75, wherein the prosthesis is balloon expandable.

In embodiments of the disclosure according to any of the above clauses, at least some of the stent structural elements are elongate and have a similar cross-section along their length or at least along a major portion of their length. In embodiments of the disclosure according to any of the above clauses, at least some of the stent structural elements have the same cross-section along their length or at least along a major portion of their length. The cross-sections of different stent structural elements may be the same, similar or different.

What is claimed is:

1. An expandable biodegradable stent prosthesis comprising:
a tubular expandable stent prosthesis body comprising a biodegradable polymeric material, said expandable stent prosthesis body comprising stent structural elements each having a luminal surface and an abluminal surface and a thickness between said luminal and abluminal surfaces; wherein the side surface regions extending between the abluminal surface and the luminal surface of at least some structural elements are bulbous, and wherein at least some of the abluminal surface regions are substantially concave and said luminal surface region is substantially flat.

2. The expandable prosthesis of claim 1, wherein a width of the stent structural elements between the side surface regions is greater at about the mid-point between said abluminal and luminal surface regions.

3. The expandable stent prosthesis of claim 1, wherein stent structural elements comprise expandable rings, each ring comprising struts joined by crowns, and each ring is connected to an adjacent ring by at least one link.

4. The expandable stent prosthesis of claim 3, wherein the prosthesis is expandable from a crimped diameter to a deployed diameter at body temperature without substantial rotation of at least one of the struts, crowns or links about their axis.

5. The expandable stent prosthesis of claim 1, wherein the stent structural elements comprise struts joined by crowns.

6. The expandable stent prosthesis of claim 5, wherein said prosthesis has been treated to shift material from the surface region of some struts and/or crowns to an immediately adjacent surface region of said strut or crown without a substantial change in body weight of said expandable stent prosthesis.

7. The expandable prosthesis of claim 1, wherein the biodegradable polymeric material of said expandable stent prosthesis body comprises at least two biodegradable polymers.

8. The expandable prosthesis of claim 1, further comprising at least some of the abluminal surface regions being substantially concave across substantially the width of said surface regions.

9. The expandable stent prosthesis of claim 8, wherein the expandable stent prosthesis body has been patterned from a tube by a laser and wherein the stent structural elements have been treated to form said substantially concave abluminal surface regions, said substantially flat luminal surface region, and bulbous side surface regions.

10. The expandable prosthesis of claim 1, wherein the expandable stent prosthesis body has been patterned from a tube by a laser.

11. The expandable stent prosthesis of claim 10, wherein the expandable prosthesis body is formed from a substantially continuous body free from discontinuities before patterning.

12. The expandable stent prosthesis of claim 1, wherein the stent structural elements have been treated to form the bulbous regions.

13. The expandable stent prosthesis of claim 12, wherein the treatment includes shaping by application of a solvent by at least one of dipping, spraying, or contact with a solvent vapor.

14. The expandable stent prosthesis of claim 12, wherein the treatment includes shaping by tumbling, agitating, deburring, scraping, media blasting, laser treatment or heat treatment.

15. The expandable stent prosthesis of claim 12, wherein a weight of the expandable stent prosthesis after treatment is substantially the same as before treatment.

16. The expandable stent prosthesis of claim 12, wherein the treatment does not dissolve the polymeric material from which said prosthesis is formed.

17. The expandable stent of claim 12, wherein the treatment comprises exposing the expandable prosthesis to a solvent for a predetermined period of time to provide substantially at least some bulbous side surface regions and at least some substantially concave abluminal surface regions of said stent structural elements.

18. The expandable stent prosthesis of claim 12, wherein the treatment causes a thickness of the plurality of stent structural elements between the luminal and abluminal surface regions to increase while decreasing a minimum width of the stent structural elements between the side surface regions by redistributing the polymeric material.

19. The expandable stent prosthesis of claim 1, further comprising a coating of at least one drug formed over at least some portions of the expandable stent prosthesis body.

20. The expandable stent prosthesis of claim 1, further comprising a coating over the expandable stent prosthesis body, said bulbous regions of said stent structural elements remaining substantially bulbous after coating.

21. The expandable prosthesis of claim 1, wherein the biodegradable polymeric material has an elastic modulus of at least 0.35 GPa.

22. The expandable stent prosthesis of claim 1, wherein the biodegradable polymeric material comprises one or more of polymers and copolymers.

23. The expandable stent prosthesis of claim 1, wherein the prosthesis is expandable from a crimped diameter to a deployed larger diameter at body temperature.

24. The expandable stent prosthesis of claim 1, wherein the biodegradable polymeric material comprises at least one material selected from the group consisting of lactides, poly-DL-Lactide, polylactide-co-glycolide, polylactide-co-polycaprolactone, poly (L-lactide-co-trimethylene carbonate), polytrimethylene carbonate, polyhydroxybutyrate, polyhydroxyvalerate, poly orthoesters, poly anhydrides, polylactide, polyglycolides, polycaprolactone, polyiminocarbonates and copolymers thereof.

25. The expandable stent prosthesis of claim 1, wherein the prosthesis is balloon expandable.

26. The expandable stent prosthesis of claim 1, wherein biodegradable polymeric material has a molecular weight ranging from 100 KDa to 1000 KDa.

27. The expandable stent prosthesis of claim 1, said body has been treated to adjust a thickness of the plurality of stent structural elements from a first thickness before treatment to a second thickness after treatment, wherein the second thickness is greater than the first thickness.

28. The expandable stent prosthesis of claim 1, wherein said body has been treated to cause a thickness of a plurality of stent structural elements between the luminal and abluminal surface regions to increase while a width of the stent structural elements between the side surface regions remains substantially the same.

29. The expandable stent prosthesis of claim 1, wherein said prosthesis has been treated by contact with a solvent to redistribute said polymeric material to provide an increased thickness of said stent structural elements and a decreased width of said stent structural elements.

30. An expandable biodegradable stent prosthesis comprising:

a tubular expandable stent prosthesis body comprising a biodegradable polymeric material, said expandable stent prosthesis body comprising stent structural elements each having a luminal surface and an abluminal surface and a thickness between said luminal and abluminal surfaces; wherein the thickness varies across the width of at least some of the structural elements, and wherein said thickness of at least some stent structural elements is greater at about an edge of said abluminal surface region than the thickness near the middle of said abluminal surface region of said structural elements and said luminal surface region is substantially flat.

31. The expandable biodegradable stent prosthesis of claim 30, wherein said prosthesis has been treated by contact with a solvent to redistribute said polymeric material to shape said structural elements.

32. The expandable biodegradable stent prosthesis of claim 30, wherein said prosthesis has been treated by contact with a solvent to redistribute said polymeric material to provide an increased thickness of said structural elements and decreased width of said structural elements.

33. The expandable stent prosthesis of claim 1 or 30, wherein said stent prosthesis further comprises radiopaque markers.

34. The expandable stent prosthesis of claim 1 or 30, wherein the stent further comprises metallic material.

35. The expandable prosthesis of claim 30, wherein the stent structural elements have two side surface regions extending between the luminal and abluminal surface regions, wherein at least some of the side surface regions are convex.

36. The expandable prosthesis of claim 35, wherein a width of the stent structural elements between the side surface regions also varies across the thickness of at least some stent structural elements.

37. The expandable prosthesis of claim 30, wherein a weight of said prosthesis after treatment is substantially the same as before treatment.

38. The expandable prosthesis of claim 30, wherein said body has been treated to cause a thickness of a plurality of stent structural elements between the luminal and abluminal surface regions to increase while a width of the stent structural elements between the side surface regions remains substantially the same.

* * * * *